(12) United States Patent
Thomas et al.

(10) Patent No.: US 7,282,624 B2
(45) Date of Patent: Oct. 16, 2007

(54) PLANT CELL DEATH SYSTEM

(75) Inventors: Christopher John Robert Thomas, Cambridge (GB); Michael John McPherson, Leeds (GB); Howard John Atkinson, Leeds (GB); Anil Neelam, Beltsville, MD (US)

(73) Assignee: Advanced Technologies (Cambridge) Limited, London (GB)

( * ) Notice: Subject to any disclaimer, the term of this patent is extended or adjusted under 35 U.S.C. 154(b) by 0 days.

(21) Appl. No.: 09/978,273

(22) Filed: Oct. 15, 2001

(65) Prior Publication Data

US 2002/0138869 A1    Sep. 26, 2002

(30) Foreign Application Priority Data

Oct. 14, 2000  (GB)  ................................ 0025225.4

(51) Int. Cl.
*C12N 15/82*    (2006.01)
*A01H 5/00*     (2006.01)

(52) U.S. Cl. ................... 800/287; 800/298; 435/320.1; 435/419

(58) Field of Classification Search ................ 800/278, 800/290, 298, 279, 287; 435/419, 468, 320.1
See application file for complete search history.

(56) References Cited

U.S. PATENT DOCUMENTS

| 5,248,606 A |   | 9/1993 | Walsh et al. |
| 5,332,808 A | * | 7/1994 | Boston et al. ............. 536/23.6 |
| 5,646,026 A |   | 7/1997 | Walsh et al. |
| 6,015,940 A |   | 1/2000 | Kaniewski et al. |

FOREIGN PATENT DOCUMENTS

| EP | 0344029    | 11/1989 |
| EP | 0 466 222  | 1/1992  |
| WO | WO89/10396 | 11/1989 |
| WO | WO92/04453 | 3/1992  |
| WO | WO92/21757 | 12/1992 |
| WO | WO93/18170 | 9/1993  |
| WO | WO94/17194 | 8/1994  |
| WO | WO97/03183 | 1/1997  |
| WO | WO97/20056 | 6/1997  |
| WO | WO98/32325 | 7/1998  |
| WO | WO99/60843 | 12/1999 |
| WO | WO 02/033106 | 4/2002 |

OTHER PUBLICATIONS

Maddaloni et al. Tolerance to the fungal pathogen *Rhizoctonia solani* AG4 of transgenic tobacco expressing the maize ribosome-inactivating protein. Transgenic Research, 1997, vol. 6, pp. 393-402.*
Hey et al. Maize ribosome-inactivating protein (b-32) homologs in related species, effects on maize ribosomes, and modulation of activity by pro-peptide deletions. Plant Physiology, 1995, vol. 107, pp. 1323-1332.*
Bass et al. Cloning and sequencing of a second ribosome-inactivating protein gene from maize (Zea mays L.). Plant Physiolog 1995, vol. 107, pp. 661-662.*
Stirpe et al. Ribosome-inactivating proteins from plants: present status and future prospects. Biotechnology, 1992, vol. 10, pp. 405-412.*
Czako et al. The herpes simplex virus thymidine kinase gene as a conditional negative-selection marker gene in *Arabidopsis thaliana*. Plant Physiology, 1994, 104:1067-1071.*
O'Keefe et al. Plant Expression of a Bacterial Cytochrome P450 That Catalyzes Activation of a Sulfonylurea Pro-Herbicide. Plant Physiology, 1994, 105:473-482.*
Tsugeki et al. Genetic ablation of root cap cells in Arabidopsis. PNAS Oct. 26, 1999, vol. 96, No. 22, pp. 12941-12946.*
Abe et al. 1987, Molecular cloning of a cysteine proteinase inhibitor of rice (oryzacystatin). Homology with animal cystatins and transient expression in the ripening process of rice seeds. J Biol Chem. 262(35):16793-7.
Barbieri et al. 1993, Ribosome-inactivating proteins from plants. Biochim Biophys Acta. 1154(3-4):237-82. Review.
Bass et al. 1992, A maize ribosome-inactivating protein is controlled by the transcriptional activator Opaque-2. Plant Cell. 4(2):225-34.
Bass et al., 1995, Cloning and sequencing of a second ribosome-inactivating protein gene from maize (Zea maize L.). Plant Physiology. 107, 661-662.
Battelli et al. 1990, Toxicity of, and histological lesions caused by, ribosome-inactivating proteins, their IgG-conjugates, and their homopolymers. APMIS. 98(7):585-93.
Chen et al. 1991, Effect of pokeweed antiviral protein (PAP) on the infection of plant viruses. Plant Pathol. 40:612-620.
Conkling et al. 1990, Isolation of transcriptionally regulated root-specific genes from tobacco Plant Physiol. 93:1203-11.
Day et al. 1998, The deoxyribonuclease activity attributed to ribosome-inactivating proteins is due to contaimination. Eur J Biochem. 258(2):540-5.
Hartley R. W., 1988, Barnase and barstar: expression of its cloned inhibitor permits expression of a cloned ribonuclease. Journal of Molecular Biology. 202:913-915.
Honjo et al. 2002, Genomic clones encoding two isoforms of pokeweed antiviral protein in seeds (PAP-S1 and S2) and the N-glycosidase activities of their recombinant proteins on ribosomes and DNA in comparison with other isoforms. J Biochem (Tokyo). 131(2):225-31.

(Continued)

*Primary Examiner*—Cynthia Collins
(74) *Attorney, Agent, or Firm*—Kenyon & Kenyon LLP

(57)  ABSTRACT

This invention seeks to provide means by which transgenic plants harbour within their genome a chimaeric gene which when expressed produces a protein having a cytotoxic effect. Cytotoxicity is achieved by way of a protein or part thereof capable of blocking cellular protein synthesis, such as a maize ribosome inactivating protein or part thereof. The chimaeric gene may comprise a promoter operably linked to a sequence encoding a protein capable of blocking cellular protein synthesis such that the promoter is inducible at and/or adjacent to a target site.

11 Claims, 11 Drawing Sheets

OTHER PUBLICATIONS

Kondo et al. 1991, Gene organization of oryzacystatin-II, a new crystatin superfamily member of plant origin, is closely related to that of oryzacystatin-I but different from those of animal cystatins. FEBS Lett. 278(1):87-90.

Lodge et al. 1993, Broad-spectrum virus resistance in transgenic plants expressing pokeweed antiviral protein. Proc Natl Acad Sci U S A. 90(15):7089-93.

Mariana et al., 1990, Induction of male sterility in plants by a chimeric ribonuclease gene. Nature 347:737-741.

Moon et al. 1997, Expression of a cDNA encoding Phytolacca insularis antiviral protein confers virus resistance on transgenic potato plants. Mol Cells. 7(6):807-15.

Perry et al., 1996, The MADS domain protein AGL15 localizes to the nucleus during early stages of seed development. The Plant Cell. 8:1977-1989.

Prestle et al. 1992, Type 1 ribosome-inactivating proteins depurinate plant 25S rRNA without species specificity. Nucleic Acids Res. 20(12):3179-82.

Rajamohan et al. 2001, Binding interactions between the active center cleft of recombinant pokeweed antiviral protein and the alpha-sarcin/ricin stem loop of ribosomal RNA. J Biol Chem. 276(26):24075-81.

Rajamohan et al. 2001, Active center cleft residues of pokeweed antiviral protein mediate its high-affinity binding to the ribosomal protein L3. Biochemistry. 40(31):9104-14.

Ready et al. 1986, Extracellular localization of pokeweed antiviral protein. Proc Natl Acad Sci U S A. 83(14):5053-6.

Richardson, M. 1991 Seed storage proteins: The enzyme inhibitors. In *Methods in Plant Biochemistry*. Dey and Harbone, eds. vol. 5, pp. 259-305.

Ryan, CA, 1991, Protease inhibitors in Plants: Genes for improving defenses against insects and pathogens. Annu. Rev. Phytopahtol. 28:425-49.

Samach et al., 1997, Divergence of function and regulation of class B floral organ identity genes. The Plant Cell. 9:559-570.

Sieburth and Meyerowitz 1997, Molecular dissection of the AGAMOUS control region shows that cis elements for spatial regulation are located intragenically. The Plant Cell. 9:355-365.

Song et al. 2000, Systemic induction of a Phytolacca insularis antiviral protein gene by mechanical wounding, jasmonic acid, and abscisic acid. Plant Mol Biol. 43(4):439-50.

Spreafico et al. 1983, The immunomodulatory activity of the plant proteins Momordica charantia inhibitor and pokeweed antiviral protein. Int J Immunopharmacol. 5(4):335-43.

Stirpe and Barbieri, 1986, Ribosome-inactivating proteins up to date. FEBS Letters 195:1-8.

Stirpe et al., 1978, Inhibition of protein synthesis by modeccin, the toxin of Modecca digitata. FEBS Letters. 85:65-67.

Stirpe et al. 1992, Ribosome-inactivating proteins from plants: present status and future prospects. Biotechnology (N Y). 10(4):405-12. Review.

Tumer et al. 1999, Pokeweed antiviral protein and its applications. Curr Top Microbiol Immunol. 240:139-58.

Tumer et al. 1997, C-terminal deletion mutant of pokeweed antiviral protein inhibits viral infection but does not depurinate host ribosomes. Proc Natl Acad Sci U S A. 94(8):3866-71.

Twell et al., 1991, Isolation and Expression of an Anther-Specific Gene From Tomato. Molecular Gen. Genet. 217:240-245.

Urwin et al. 1995, Engineered oryzacystatin-I expressed in transgenic hairy roots confers resistance to Globodera pallida. Plant J. 8(1):121-31.

Wang et al. 2000, Virus resistance mediated by ribosome inactivating proteins. Adv Virus Res. 55:325-55. Review.

Wang et al. 1998, Reduced toxicity and broad spectrum resistance to viral and fungal infection in transgenic plants expressing pokeweed antiviral protein II. Plant Mol Biol. 38(6):957-64.

Wang et al. 1999, Pokeweed antiviral protein cleaves double-stranded supercoiled DNA using the same active site required to depurinate rRNA. Nucleic Acids Res. 27(8):1900-5.

Watanabe et al. 1997, Actions of pokeweed antiviral protein on virus-infected protoplasts. Biosci Biotechnol Biochem. 61(6):994-7.

Yeung et al. 1988, Trichosanthin, alpha-momorcharin and beta-momorcharin: identity of abortifacient and ribosome-inactivating proteins. Int J Pept Protein Res. 31(3):265-8.

Zoubenko et al. 2000, A non-toxic pokeweed antiviral protein mutant inhibits pathogen infection via a novel salicylic acid-independent pathway. Plant Mol Biol. 44(2):219-29.

Zoubenko et al. 1997, Plant resistance to fungal infection induced by nontoxic pokeweed antiviral protein mutants. Nat Biotechnol. 15(10):992-6.

Cho et al. 1999, Isolation and Characterization of eDNAs Encoding Ribosome Activating Protein from Dianthus sinensis L. Mol. Cells. 10(2): 135-141.

International Search Report dated May 13, 2002 for PCT/GB01/04581.

* cited by examiner

TA29-BAR-Nos in pBI121

TA29-RIP-Nos in pBI121

PLANT CELL DEATH SYSTEM

The present invention relates to a plant cell death system, and in particular to transgenic plants which harbour within their genome a chimaeric gene which when expressed produces a cytotoxic protein.

One of the means open to plant breeders attempting to produce new cultivars is the production of hybrids between existing cultivars containing desirable traits. Hybrids are generally superior in a variety of characteristics to either parent, a phenomenon known as hybrid vigour. Such hybrid crosses may be performed by manual cross pollination, a tedious and time consuming procedure.

During the production of such hybrid crosses the prevention of self pollination is vital. To achieve this, the female parent may be emasculated by hand, e.g. in the production of hybrid corn by de-tasseling. However, the large scale emasculation of species with hermaphrodite flowers is economically unfeasible. Female parent lines (male sterile) may also be generated by genetic male sterility, a known trait in many plants, usually being recessive and monogenic. The problem with this approach is that it is difficult to obtain pure lines of male sterile parents for every cross. The most widely used system of producing male sterility for use in hybrid production is cytoplasmic male sterility (cms). In this case cytoplasmic factors are responsible for pollen abortion. In crops where cms has been identified in the germplasm it has been used extensively e.g. maize, sunflower. There are several disadvantages of the system: male sterile cytoplasm may be associated with other undesirable characteristics e.g. T-cytoplasm in maize and susceptibility to *Helminthosporium maydis*; its application requires isogenic maintainer male fertile lines to propagate the male parent; and it is limited to species in which a cytoplasmic source of sterility is available.

Another advantage of a male sterility system would be the production of pollen-free plants. This would be desirable in a number of ornamental flower varieties, and would also have application in the containment of genetic traits by the prevention of outcrossing.

A further desirable property of a sterility system is that female sterile plants could be produced such that fruit development would occur in the absence of seed set. Seedless fruit varieties would be advantageous for processing, e.g. tomatoes, and also desirable to the consumer, e.g. melon. Seedless varieties are available and there are established breeding programmes, but the development of seedless fruit has been limited by the availability of the appropriate germplasm in many species.

In cases where a genetic source of sterility is not available or is otherwise unfeasible, a genetic modification approach could provide sterility by providing a cell death system whereby necrosis occurs in specific cells in the reproductive tissues.

WO 89/10396 discloses a plant cell death system wherein a chimaeric gene is introduced into a plant, which chimaeric gene comprises an anther specific promoter attached to a RNAse protein or polypeptide which, when expressed, causes disruption of cell metabolism. Thus, expression of the chimaeric gene results in necrosis of the anther cells and results in male sterility in the plants.

The present cell death system could be used to provide female sterility in plants, whereby the target site may be the ovule of the plant.

WO 93/18170 and WO 92/04453 disclose plant cell death systems which are specific to controlling nematode infection. In WO 93/18170 and WO 92/04453 a gene comprising a coding sequence, which coding sequence encodes for a product which is disruptive of nematode attack is introduced into a host plant species. The gene further comprises a promoter region, which promoter region controls the expression of the coding sequence such that expression occurs upon nematode attack and substantially specifically within or adjacent to the nematode feeding site cells. In order to disrupt nematode attack, the product may be either inimical to the plant cells which differentiate into nematode feeding site cells or cells adjacent thereto, or inimical to the nematodes directly.

Economically important plant parasitic nematodes include cyst nematodes, such as potato cyst nematodes (*Globodera rostochiensis* and *G. pallida*), soybean cyst nematode (*Heterodera glycines*), beet cyst nematode (*Heterodera schachtii*) and cereal cyst nematode (*Heterodera avenae*), and root knot nematodes, such as *Meloidogyne* spp. Such plant parasitic nematodes are major pathogens of many crops world-wide, for example vegetables, food legumes, tomato, water melon, grape, peanut, tobacco and cotton.

Chemical control, cultural practices and the use of resistant plant varieties are the chief approaches to nematode control which are currently available and they are often used in an integrated manner against plant parasitic nematodes. There is a requirement for improvement in nematode control because these current approaches offer inadequate crop protection. Nematicides are of questionable environmental status and they are not always efficacious. Cultural control imposes hidden losses on growers in several ways. The wide host range of root knot nematodes limits the availability of economically satisfactory non-host crops. Effective resistant cultivars are frequently unavailable and those that the grower can use are sometimes out-performed by susceptible cultivars at low nematode densities. Also resistance may be lost in the high soil temperatures that occur in tropical and sub-tropical environments.

Other applications of plant cell death systems can be envisioned. For example the target site may be specific parts of the flower, thereby altering the morphology of the flower. Alternatively the target site may be lateral roots, thorns or stinging hairs. Abscission of leaf or fruit might be achieved by the targeting the abscission zone of the leaf or the fruit. Facilitating the release of seeds from plants, by targeting the funicle might be achievable. By targeting other organs such as trichomes, which trichomes are typically glandular, the production of chemical substances by the trichomes can be cessated or prevented. Another application might be the inducible abscission of roots, leaves, flowers, or fruit at the end of the growing season.

Ribosome-inactivating proteins (RIPs) are a group of toxic plant proteins that catalytically inactivate eukaryotic ribosomes (Stirpe and Barbieri 1986). RIPs function as N-glycosidases to remove a specific adenine in a conserved loop of the large rRNA, and thereby prevent binding of Elongation Factor 2, thus blocking cellular protein synthesis.

Three forms of RIPs have been described. Type 1 RIPs such as pokeweed antiviral protein and barley translation inhibitor are each comprised of a single polypeptide chain, each with an approximate $M_r$ value of 30,000. Type 2 RIPs such as ricin, abrin and modeccin each comprise two polypeptide chains; one polypeptide with RIP activity (A-chain) is linked by a disulphide bond to a galactose-binding lectin (B-chain; Stirpe et al 1978). The $M_r$ value of each Type 2 RIP is approximately 60,000.

Maize RIP, which is found in the endosperm of maize (*Zea mays*) seeds, is a Type 3 RIP. This RIP is synthesised as a single polypeptide chain, but subsequently undergoes proteolytic cleavage to release two active peptide domains. Maize RIP comprises two domains the α domain and the β domain, which domains are separated in the inactive form of maize-RIP (i.e. maize pro-RIP) by a central peptide spacer and are flanked by N and C terminal peptides. The α domain is located towards the N terminus of the pro-RIP; the β domain is located towards the C terminus. During seed germination, the maize pro-RIP is activated by proteolytic cleavage of the N and C terminal peptides together with the central peptide spacer such that the two domains form the mature (active) maize RIP (U.S. Pat. No. 5,248,606). Cleavage is effected by endogenous proteases.

The present invention provides a method of producing a transgenic plant which harbours within the genome of the plant a chimaeric gene, the expression of which gene causes plant cytotoxicity, wherein a plant is transformed with a chimaeric gene comprising a promoter, which promoter is induced at and/or adjacent to a target site, operably linked to a coding sequence, which coding sequence encodes a maize ribosome inactivating protein or a part thereof.

As used herein "part" means a part of the gene coding for maize RIP, which part is active in inhibiting protein synthesis.

The present invention further provides a plant transformed with a chimaeric gene comprising a promoter, which promoter is induced at and/or adjacent to a target site, operably linked to a coding sequence, which coding sequence encodes a maize ribosome inactivating protein or a part thereof.

The present invention yet further provides a plant cell transformed with a chimaeric gene comprising a promoter, which promoter is induced at and/or adjacent to a target site, operably linked to a coding sequence, which coding sequence encodes a maize ribosome inactivating protein or a part thereof.

The present invention also provides a DNA isolate of a chimaeric gene comprising a promoter, which promoter is induced at and/or adjacent to a target site, operably linked to a coding sequence, which coding sequence encodes a maize ribosome inactivating protein or a part thereof.

The present invention further provides a biologically functional expression vehicle containing a chimaeric gene comprising a promoter, which promoter is induced at and/or adjacent to a target site, operably linked to a coding sequence, which coding sequence encodes a maize ribosome inactivating protein or a part thereof.

The coding sequence of the maize ribosome inactivating protein disclosed in this invention may comprise the entire pro-RIP sequence as described above comprising the N-terminal peptide, the α domain, the central spacer peptide, the β domain, and the C-terminal peptide.

The coding sequence of the maize ribosome inactivating protein may alternatively comprise a recombinant "mature" RIP, described herein as "RIP-P", comprising the α domain and the β domain arranged contiguously, i.e. the N- and C-terminal extensions and the central spacer peptide are removed. The present invention demonstrates that the provision of a functionally active RIP molecule is not dependent upon any conformational constraints placed upon it by the intact pro-RIP molecule or by the cleavage reaction. Functional activity in cell-free translation systems of recombinant RIP molecules lacking the central spacer and terminal peptides has been described in U.S. Pat. Nos. 5,248,606 and 5,646,026.

The coding sequence of the maize ribosome inactivating protein may preferably otherwise comprise a recombinant RIP comprising the α domain only, or a recombinant RIP comprising the β domain only, the α domain or β domain alone being a part of the maize ribosome activating protein having the required functionality. The α domain of the maize ribosome inactivating protein is that domain which is situated towards the N terminal end of the maize ribosome inactivating protein, whilst the β domain of the maize ribosome inactivating protein is that domain which is situated towards the C terminal end of the maize ribosome inactivating protein. If additional nucleic acids are included in the α or β domain, then the active part will usually still be only the α or β domain.

Without wishing to be bound by theory the α domain is thought to comprise ribosome recognition and binding regions, whereas the β domain is thought to comprise the catalytic site necessary for depurination/cleavage of the ribosome. Prior to the present invention it was thought that the β domain was essential to provide an active maize ribosome inactivating protein. Thus, it was surprising to find that the inclusion of the α domain alone (i.e. without the β domain) could be used to disrupt plant ribosome function and result in plant cell necrosis.

The nucleotide sequence of the pro-RIP coding sequence is that identified in SEQ.ID.No.: 1 or a coding sequence which is homologous thereto; the nucleotide sequence of the RIP-P coding sequence is that identified in SEQ.ID.No.: 2 or a coding sequence which is homologous thereto; the nucleotide sequence of the α domain coding sequence is that identified in SEQ.ID.No.: 3 or a coding sequence which is homologous thereto; the nucleotide sequence of the β domain coding sequence is that identified in SEQ.ID.No.: 4 or a coding sequence which is homologous thereto.

Depending on the homology of the nucleotide sequences required, different conditions of stringencies may be used in the hybridisation procedure used to screen for similar sequences. By way of example and not limitation, hybridisation procedures using conditions of high stringency are as follows: hybridisation to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel P. M. et al, eds., 1989, Current Protocols in Molecular Biology, Vol. I, Green Publishing Associates, Inc., and John Wiley and Sons, Inc., New York, at p. 2.10.3). Other conditions of high stringency which may be used are well known in the art. Hybridisation procedures using conditions of moderate stringency that may be used are as follows: hybridisation to filter-bound DNA in 0.5 M $NaHPO_4$, 7% sodium dodecyl sulfate (SDS), 1 mM EDTA at 65° C., and washing in 0.2×SSC/0.1% SDS at 42° C. (Ausubel et al, 1989, supra). Other conditions of moderate stringency which may be used are well-known in the art. Other solutions such as Standard Saline Citrate (SSC) or (Saline Sodium Phosphate EDTA) (SSPE) can be used in the hybridisation procedures.

Suitable homologous sequences are sequences that are at least 70%, preferably 80% and more preferably 85%, and even more preferably 90% or 95% homologous with each sequence listed herein, which such homologous sequences retain the required enzymatic activity.

Suitable sequences may also be variants thereof. Variant in relation to the present invention may mean any substitution of, variation of, modification of, replacement of or deletion of or the addition of one or more nucleic acid(s)/ amino acids from or to the sequence, providing the resulting sequence expresses or exhibits the required enzymatic activity. A derivative or mutation may also be suitable in the invention. A derivative has some modifications, usually chemical, compared with the naturally-occurring polypeptide expressed by the nucleic acid.

Suitably, the chimaeric gene further comprises a 3' untranslated, terminator sequence. The terminator sequence may be obtained from plant, bacterial or viral genes. Suitable terminator sequences are the pea rbcS E9 terminator sequence, the nos terminator sequence derived from the nopaline synthase gene of *Agrobacterium tumefaciens* and the 35S terminator sequence from cauliflower mosaic virus, for example. A person skilled in the art will be readily aware of other suitable terminator sequences. In addition, the chimaeric gene may optionally comprise transcriptional or translational enhancer sequences, such as those described in International Patent Application, Publication No. WO 97/20056, intracellular targeting sequences and introns, for example, as well as nucleotide sequences operable to facilitate the transformation process and the stable expression of the chimaeric gene, such as T-DNA border regions, matrix attachment regions and excision/recombinant sequences.

The present invention also provides a two-component system to achieve cell death. Such two-component systems are described in International Patent Applications WO 98/32325 and WO 93/18170 whereby two or more transgenes are employed such that the combined effects of their expression products lead to cell death. The individual components are inactive or harmless in isolation, but exhibit a cytotoxic effect when present together. Each transgene is driven by a separate promoter, the promoters being selected such that their expression profiles overlap at the desired target site of cell death, but not in other tissues. The present invention describes a two-component system comprising separately the α domain and the β domain of maize ribosomal inactivating protein, each as a separate transgene construct driven by a separate promoter. Examples of suitable promoters are described below and others will be known to those skilled in the art. Such a two-component system may be produced by the crossing of two plants each containing one component, by the stacking of transgenes through sequential or simultaneous transformation with two transgene constructs, or by transformation with a construct containing both components in a single cassette. The two domains may be from different maize ribosome inactivating proteins.

Preferably, the promoter is induced specifically or substantially specifically at and/or adjacent to the target site. If the promoter is induced other than at the target site and/or the cells adjacent to the target site, the promoter is preferably predominantly expressed at the target site and/or adjacent thereto.

In accordance with a first embodiment of the present invention, the target site may be a nematode feeding site. When it is the case that the target site is a nematode feeding site, the promoter selected is one which is induced at and/or adjacent to the nematode feeding site. Such a promoter is preferably induced upon nematode infection of the plant. An example of a suitable promoter is the KNT1 promoter. The isolation of the KNT1 promoter is described in NZ Patent No. 260511 and the method is further recited below. Other suitable promoters include the TobRB7 promoter and the Lemmi promoters. The isolation of the TobRB7 promoter is taught in International Patent Application WO 94/17194, and the isolation of the Lemmi promoters are disclosed in International Patent Application WO 92/21757.

The nematode feeding site may be comprised of, for example, plant cells at the local site of infection which later redifferentiate to form a syncytium (in the case of cyst nematodes) or the giant cells and/or the accompanying hypertrophic cells (in the case of root knot nematodes), and/or one or more of the syncytium cells, the giant cells and the accompanying hypertrophic cells.

By targeting the nematode feeding site a nematode resistant plant may be obtained. By the term "nematode resistant plant" it is meant a plant which upon infection by plant parasitic nematodes is capable of preventing, slowing or otherwise adversely affecting the growth and development of nematodes that attack the plant, thereby preventing economically significant densities of plant parasitic nematodes from building up during a single crop growing period. That is to say that the nematodes may, for example, die or the nematodes' life cycle may be slowed resulting in a delay in the time taken to reach maturity and hence produce eggs, or the mature female nematodes may be of reduced size and thus have a lower egg-laying capacity as egg laying only commences after female nematodes have reached a critical, minimum size.

The present invention is applicable to, but in no way limited to, use with the following nematode species: *Globodera* spp., *Heterodera* spp. and *Meloidogyne* spp.

In accordance with a second aspect of the present invention, instead of nematode resistance the method is directed to effecting male sterility in plants. For example, the target site may be one or more of a plant's pollen, anther or tapetum. When it is the case that the target site is tapetum for example, the promoter selected is one that is induced in and/or adjacent to the tapetum. An example of a suitable tapetum promoter is the tobacco TA29 promoter as disclosed in Mariani et al (1990). Anther specific promoters are disclosed in Twell et al (1991).

In accordance with a third aspect of the present invention, the method is directed to effecting female sterility in plants. For example, the target site may be the ovule of the plant. That is to say, the promoter selected is one that is induced in and/or adjacent to the ovule. An example of a suitable promoter is the AGL15 promoter as disclosed in Perry et al, 1996.

According to a fourth aspect of the present invention, the morphology of the flower of a plant is manipulated. For example, the target site may be specific parts of the flower, the aim being that when these specific parts of the flower do not develop the morphology of the flower is changed. In that instance, the promoter selected is one that is induced in and/or adjacent to the sepal, carpel, petal, and/or stamen. Examples of suitable promoters are those found in the agamous, apetala3, globosa, pistillata and deficiens genes (Sieburth and Meyerowitz, 1997; Samach et al, 1997 and references therein).

In accordance with a fifth aspect of the present invention, the method is used to assist in or promote leaf and/or fruit abscission in plants. For example, the target site may be the abscission zone of the leaf and/or the fruit. Thus, the promoter selected is one that is induced in and/or adjacent to such an abscission zone.

A sixth aspect of the present invention is the targeting of trichomes, which trichomes are typically glandular. The promoter selected is one that is induced in and/or adjacent to the trichomes. By causing necrosis of the trichomes of the plant the production of chemical substances by the trichome can be cessated or prevented. A seventh aspect of the present invention is the targeting of lateral roots, thorns or stinging hairs.

In accordance with an eighth aspect of the present invention the method is directed to the control of virus infections. During virus infections there are a number of genes which are induced specifically, or substantially specifically, within the cells actually infected by the virus. The promoter selected is one that is induced in and/or adjacent to the cells infected by the virus.

According to a ninth aspect of the present invention the method is directed to facilitating the release of seeds from plants, by targeting the seeds. During seed development there are a number of genes which are induced specifically, or substantially specifically, within certain cells/parts of the seed.

In accordance with a tenth aspect of the present invention a promoter that is externally inducible and that is induced in, for example, the roots of the plant is selected. Such a promoter could be used to effect root abscission at the end of a growing season. Comparable promoters induced in, for example, leaf petioles, pedicels or peduncles, could be used to effect abscission of leaves, flowers, or fruit at the end of the growing season.

Techniques for transforming plants are well known within the art and include *Agrobacterium*-mediated transformation, for example. Typically, in *Agrobacterium*-mediated transformation a binary vector carrying a foreign DNA of interest, i.e. a chimaeric gene, is transferred from an appropriate *Agrobacterium* strain to a target plant by the co-cultivation of the *Agrobacterium* with explants from the target plant. Transformed plant tissue is then regenerated on selection media, which selection media comprises a selectable marker and plant growth hormones.

Further suitable transformation methods include direct gene transfer into protoplasts using polyethylene glycol or electroporation techniques, particle bombardment, microinjection and the use of silicon carbide fibres for example.

Suitable plant species which may be transformed in accordance with the present invention include, but are not limited to, rice, wheat, maize, potato, tobacco, sugar beet, soybean, canola, tomato, peanut, cotton, vine, watermelon, papaya, vegetables and food legumes.

In order that the invention may be easily understood and readily carried into effect, reference will now be made, by way of example, to the accompanying diagrammatic drawings, in which.

Figure 14:
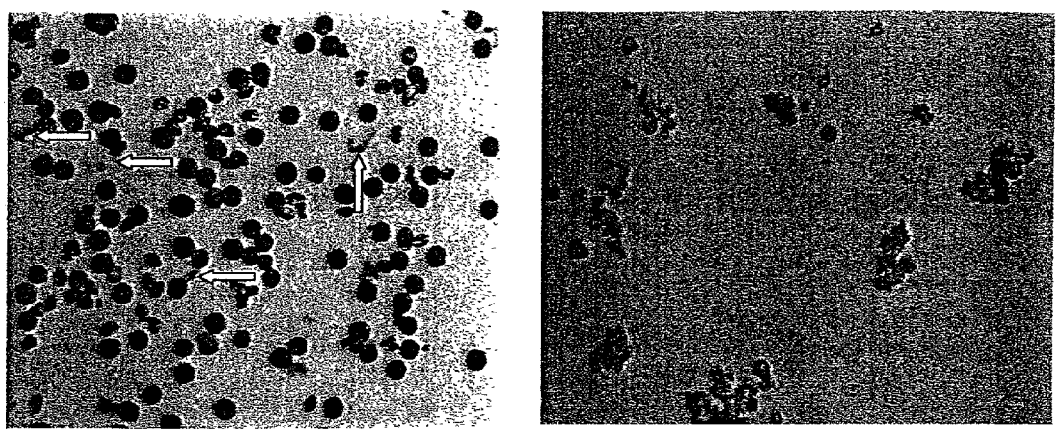
Figure 15:
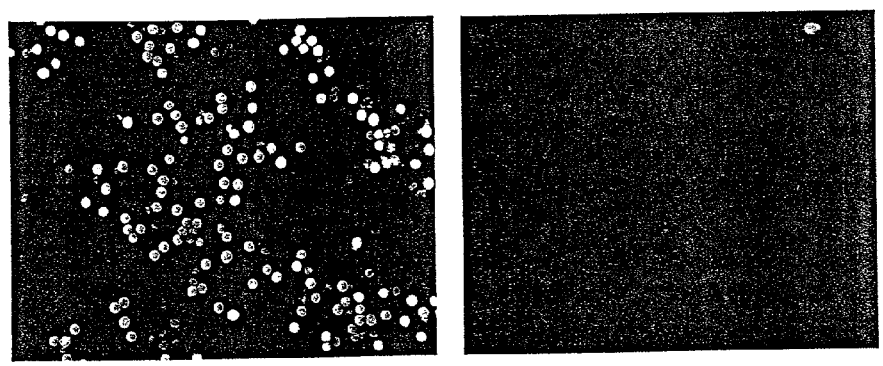

FIG. 14 shows pollen tube formation for wild-type pollen (left) with germination tubes arrowed and the RIP-P transgenic (right) with deformed pollen grain lacking germination tubes; and FIG. 15 shows wild-type pollen from cv Desiree (left) showing uptake of FDA by viable pollen grains and a similar number of pollen grains from the transgenic RIP-P line (right) showing only one with uptake of FDA. The pollen grains have a diameter of 50 μm.

EXAMPLES

Cloning and Sequencing of the Maize Ribosome Inactivating Protein

Genomic DNA was extracted from 14 day-old seedlings of maize variety Earli King.

Figure 12:
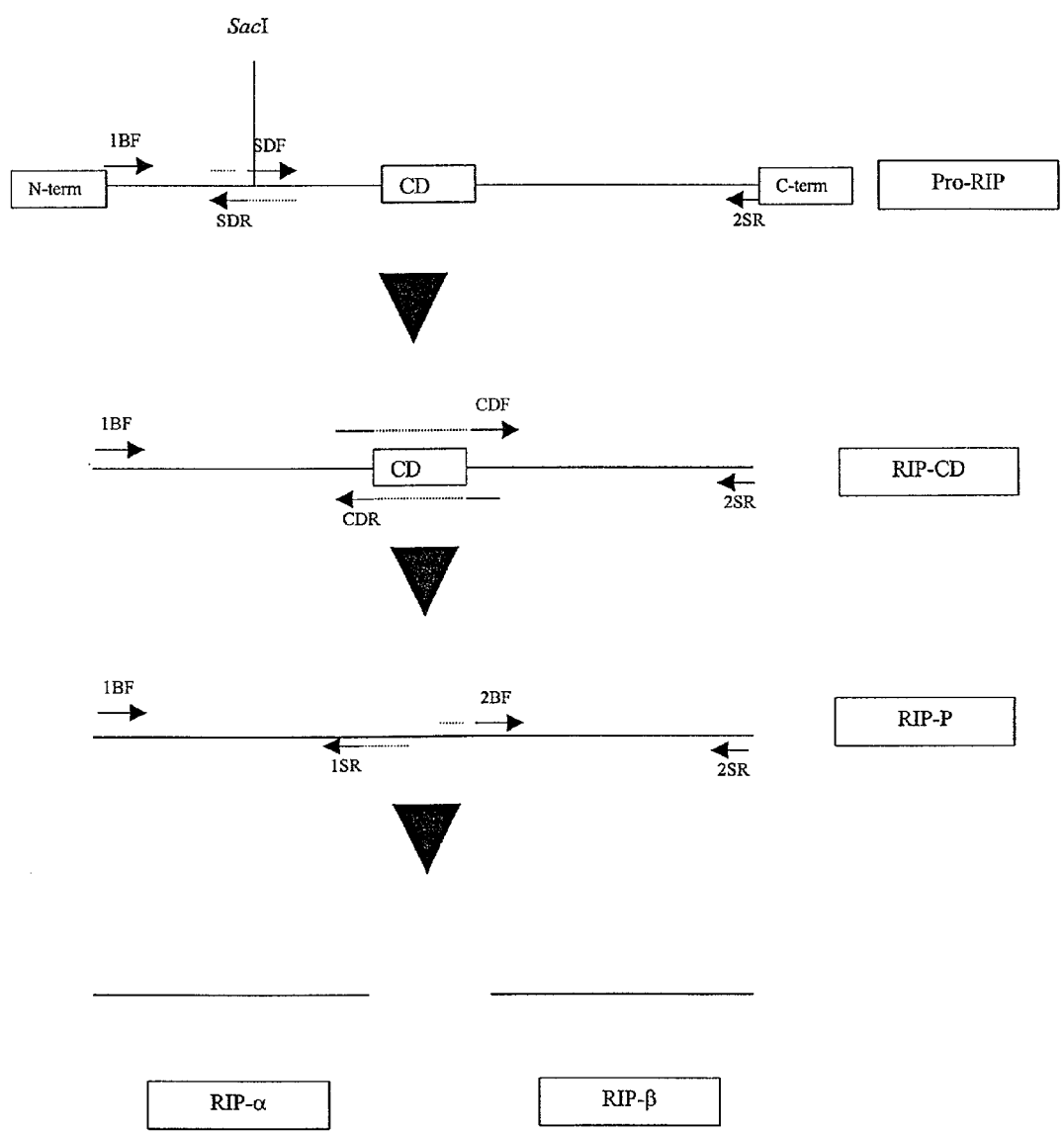
FIG. 12 is a schematic diagram of the production of maize ribosome inactivating protein variants by PCR.

Primers were designed from the nucleotide sequence of maize RIP genomic DNA to generate variants of RIP sequences, by eliminating the N- and C-terminal regions and central spacer. The primers were also designed to remove a SacI restriction site in the RIP sequence and so facilitate cloning (FIG. 12). RIP sequences were amplified with Pfu polymerase.

The PrORIP sequence (SEQ. ID. No.: 1) was obtained by PCR of the genomic DNA as follows:

To remove the SacI restriction site in the gene, two PCR reactions were performed using primers PRORIPBF (SEQ. ID. No.: 5) plus RIPSDR (SEQ. ID. No.: 14), and RIPSDF (SEQ. ID. No.: 13) plus PRORIPSR (SEQ. ID. No.: 6) respectively. The PCR products were gel purified and combined. Overlap extension followed by PCR amplification using primers PRORIPBF (SEQ. ID. No.: 5) and PRORIPSR (SEQ. ID. No.: 6) resulted in the full length ProRIP sequence (SEQ. ID. No.: 1).

PCR of ProRIP with primers RIP1BF (SEQ. ID. No.: 7) and RIP2SR (SEQ. ID. No.: 8) resulted in a PCR product of approximately 800 bp, corresponding to the RIPα, central spacer and RIPβ domains. This product ("RIP-CD") was digested with restriction endonucleases XbaI and SalI, gel purified, ligated into the vector pBluescript, transformed into *E.coli* XL1-Blue cells, and sequenced. The sequence was identical to that of the equivalent region of the maize RIP DNA.

The central spacer region was removed as follows: The RIP-CD DNA was amplified in two PCR reactions using the primers RIP1BF (SEQ. ID. No.: 7) plus RIPCDR (SEQ. ID. No.: 12) and RIPCDF (SEQ. ID. No.: 11) plus RIP2SR (SEQ. ID. No.: 8). The PCR products were gel purified and combined. Overlap extension followed by PCR with primers RIP1BF (SEQ. ID. No.: 7) and RIP2SR (SEQ. ID. No.: 8) resulted in the fully processed RIP (RIP-P). RIP-P was digested with restriction endonucleases XbaI and SalI, gel purified, ligated into the vector pBluescript, transformed into *E.coli* XL1-Blue cells, and sequenced. The RIP-P sequence is identified herein as SEQ. ID. No.: 2.

Further PCR reactions were carried out on RIP-CD using either primers RIP1BF (SEQ. ID. No.: 7) plus RIP1SR (SEQ. ID. No.: 9) or primers RIP2BF (SEQ. ID. No.: 10) plus RIP2SR (SEQ. ID. No.: 8), to amplify the RIPα or RIPβ domains respectively. RIPα or RIPβ was digested with restriction endonucleases XbaI and SalI, gel purified, ligated into the vector pBluescript, transformed into E.coli XL1-Blue cells and sequenced. The sequences of RIPα and RIPβ are identified as SEQ. ID. No.: 3 and SEQ. ID. No.: 4 respectively.

Figure 1:
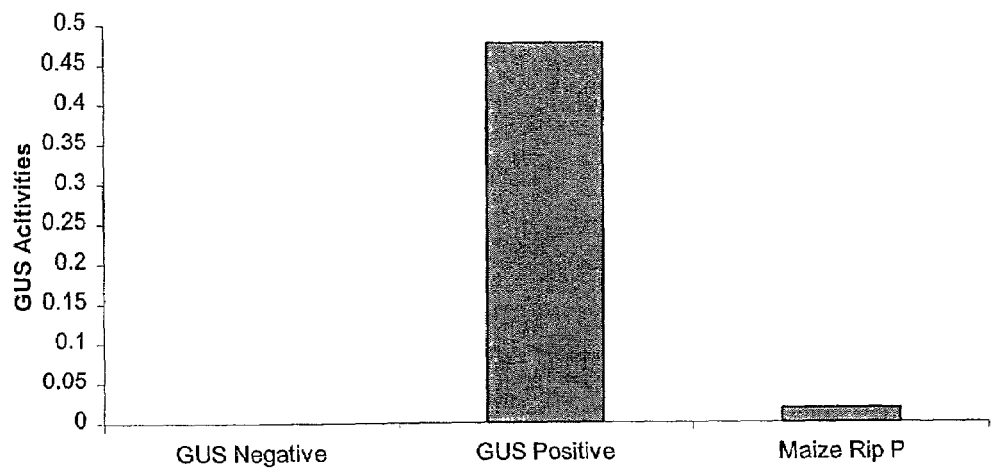
FIG. 1 shows the effect of mature maize ribosome inactivating protein (RIP-P) activity on tobacco ribosomes as measured by GUS protein synthesis.
Figure 2:
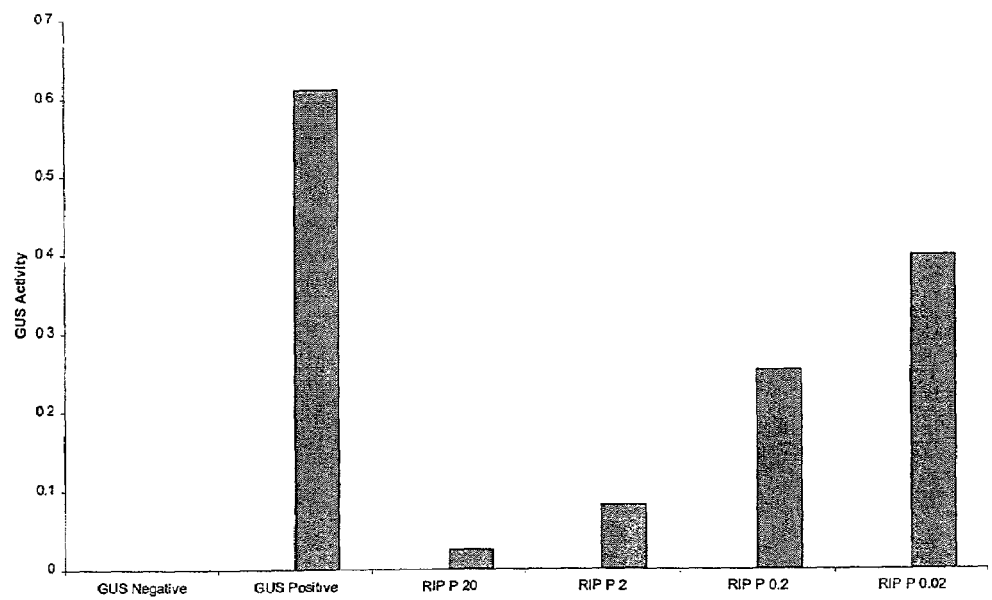
FIG. 2 shows the dosage effect of different amounts of maize RIP-P DNA (20 μg to 0.02 μg) on tobacco ribosomes as measured by GUS protein synthesis.
Figure 3:
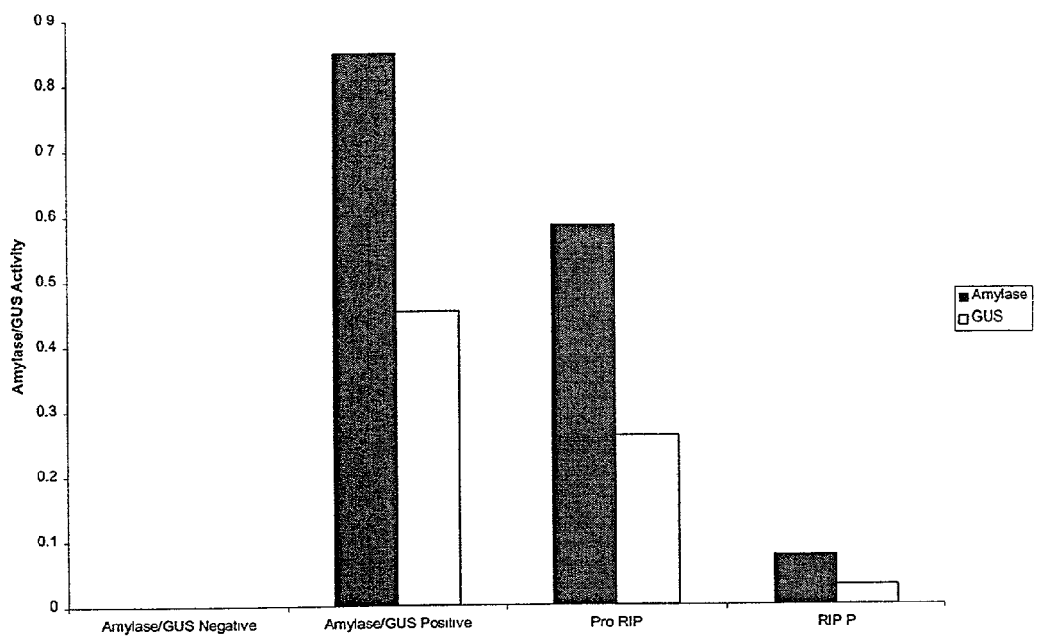
FIG. 3 shows the effect of maize RIP-P proteins on tobacco ribosomes as measured by α-Amylase and GUS protein synthesis.
Figure 4:
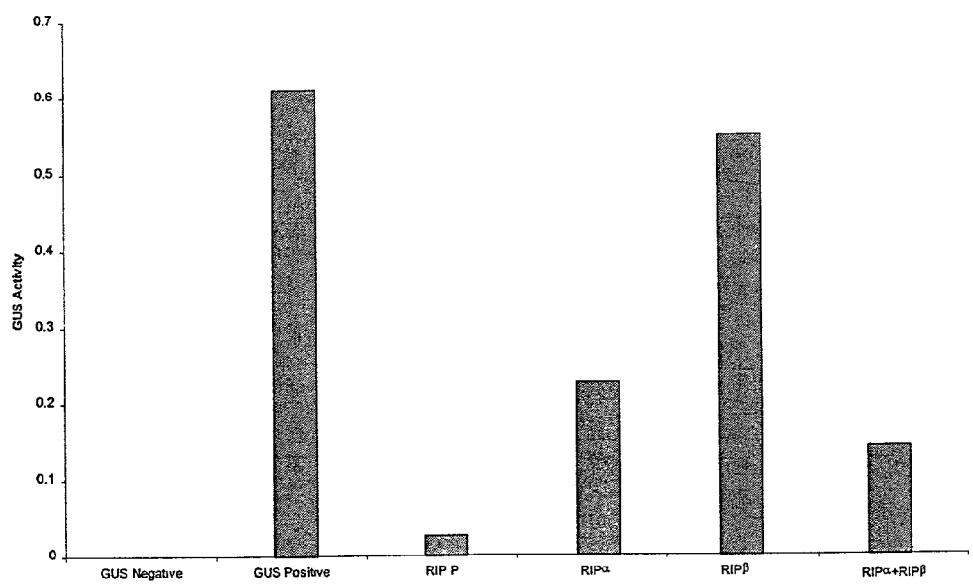
FIG. 4 shows the effect of separate maize RIP α and β domains and combined α and β domains on tobacco ribosomes as measured by GUS protein synthesis.
Figure 5:
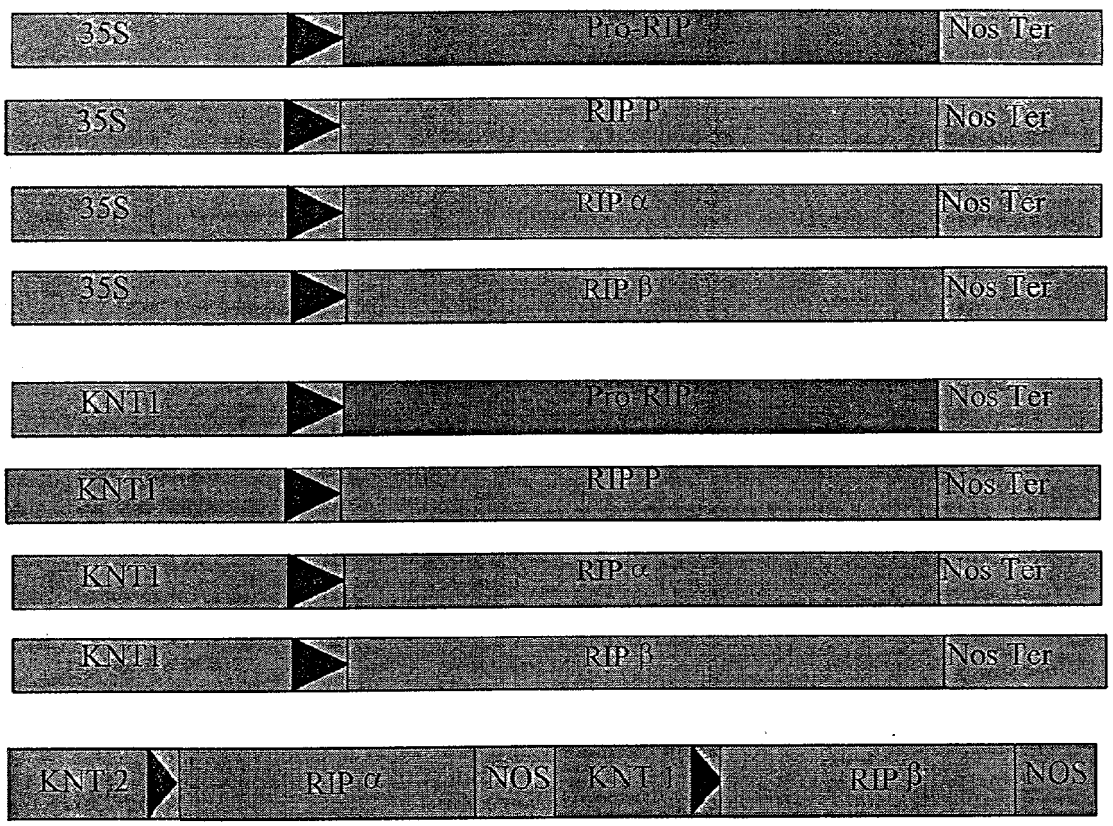
FIG. 5 shows in schematic form the pDVM35S and PATC KNT1 promoter constructs and the PATC KNT2/RIP α: KNT1/RIP β constructs used in plant transformation.
Figure 6:
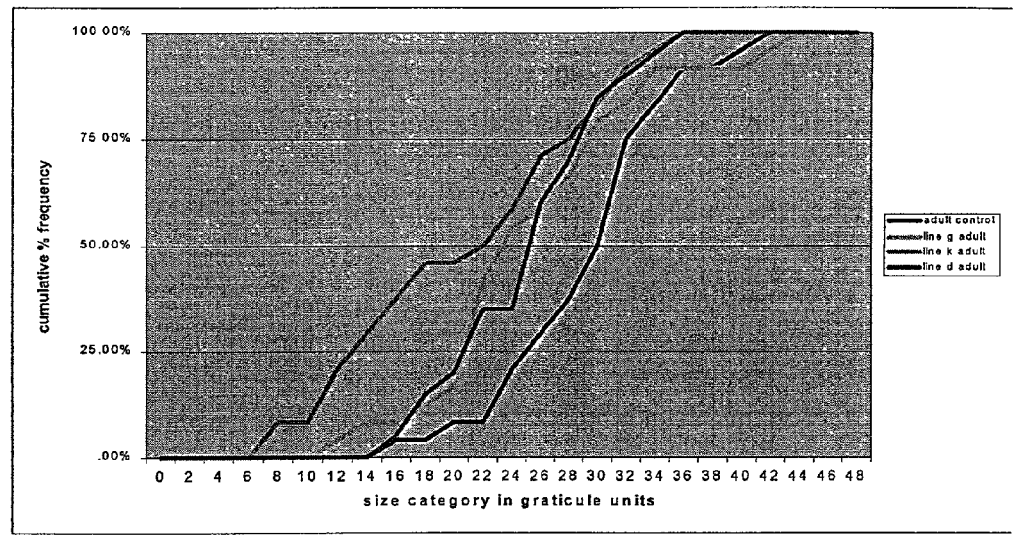
FIG. 6 shows adult nematode sizes in control and transgenic maize RIP lines plotted as a cumulative frequency graph.
Figure 7:
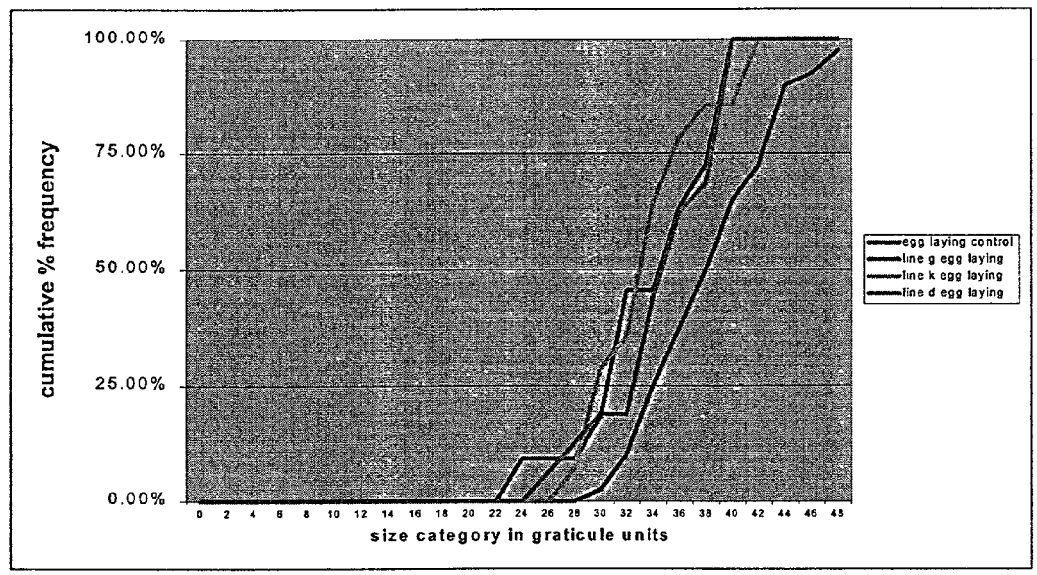
FIG. 7 shows egg-laying female sizes in the same control and transgenic maize RIP lines as FIG. 6 plotted as a cumulative frequency graph.
Figure 8:
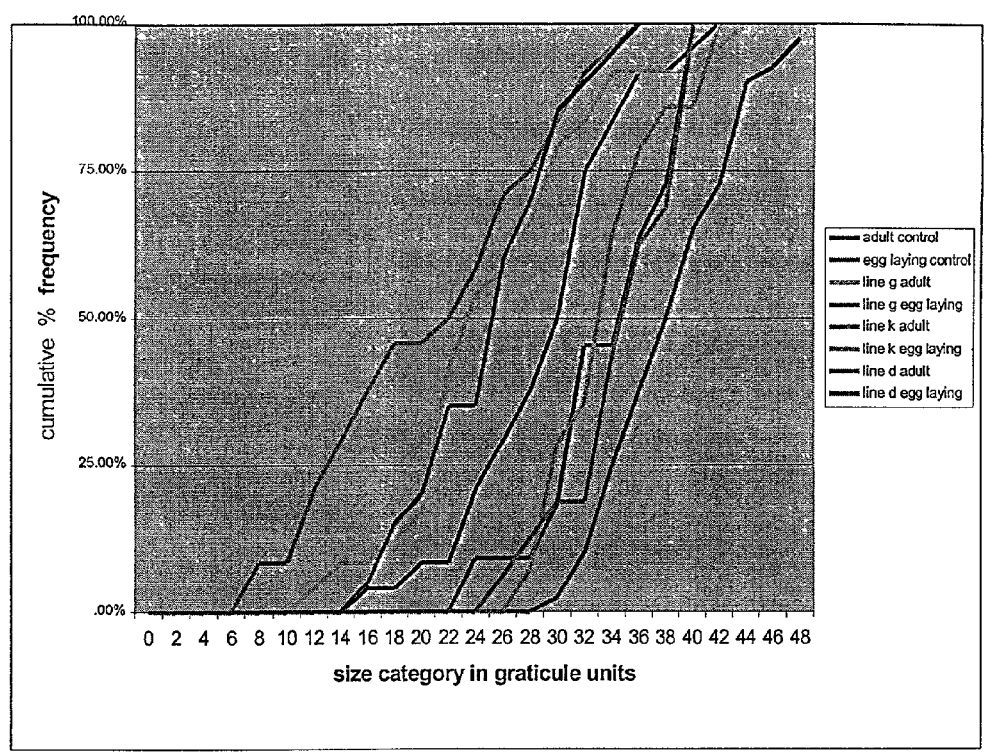
FIG. 8 shows a comparison between the sizes of adult and egg-laying root knot nematodes in control and transgenic lines plotted as a cumulative frequency graph.
Figure 9:
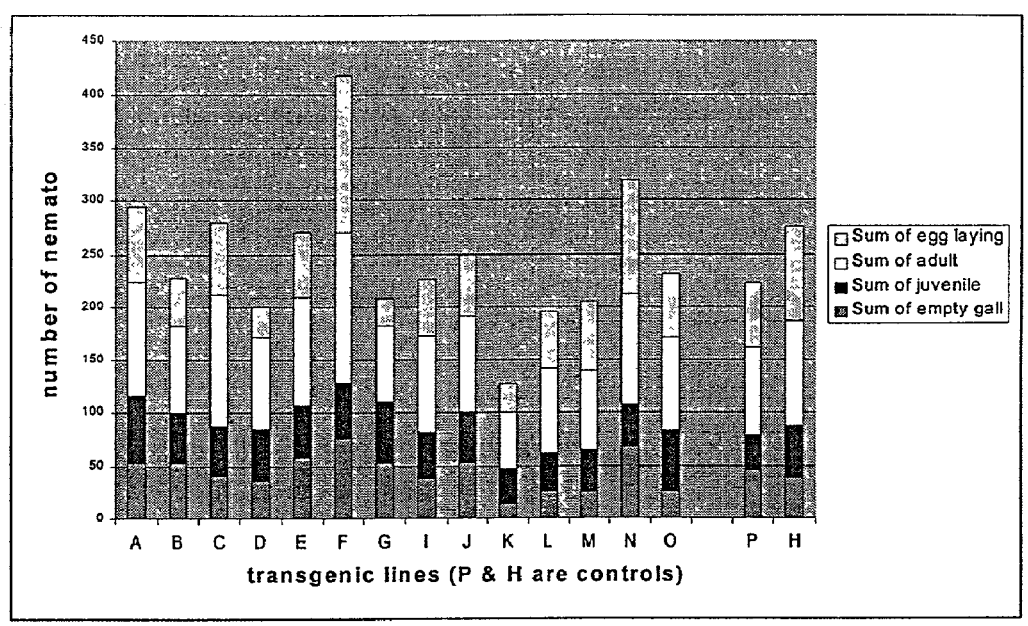
FIG. 9 shows the number of galls and three categories of nematodes for each transgenic nematode line. Lines A to G are progeny from maize RIP-P transformants, lines I to O are progeny from two-component maize RIPα/RIPβ transformants and lines P and H are untransformed control lines.
Figure 10:
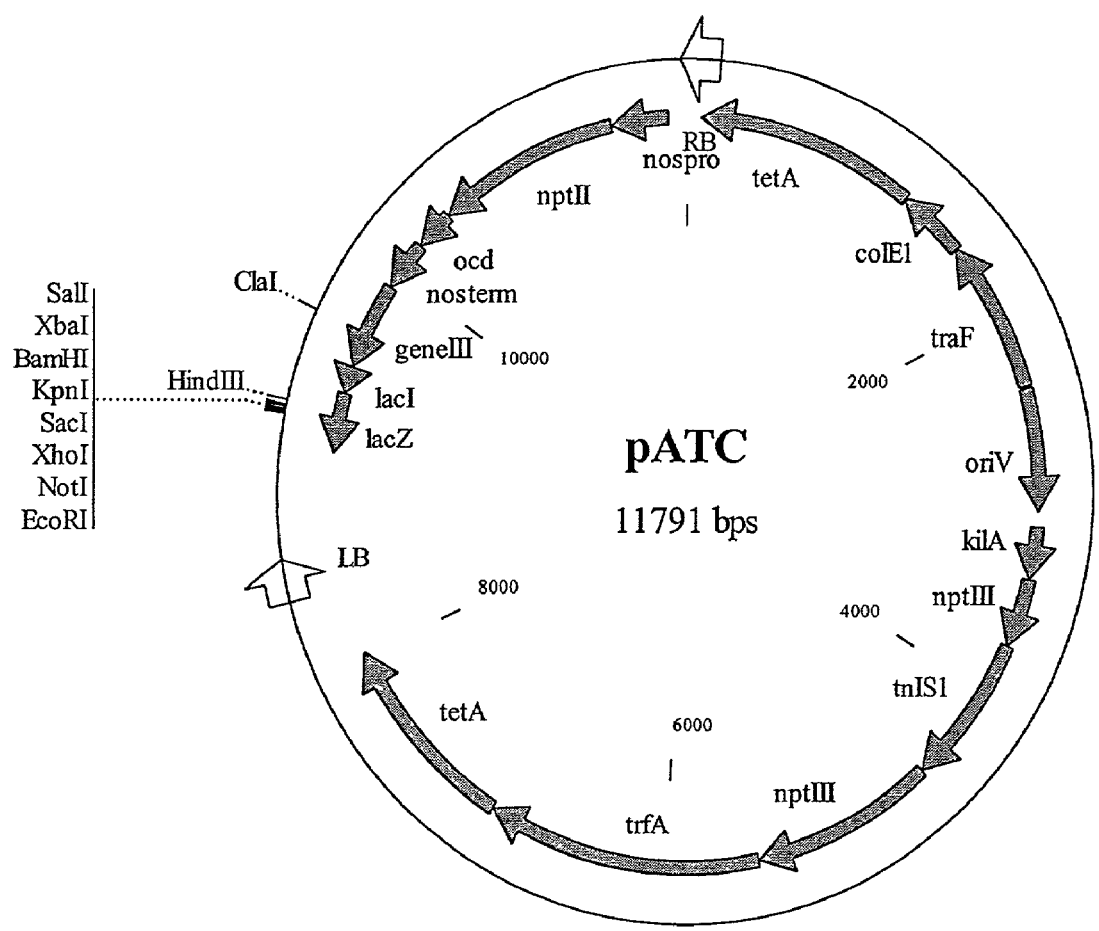
FIG. 10 shows the pATC transformation vector into which the RIP constructs of FIG. 5 were inserted for plant transformation.
Figure 11:
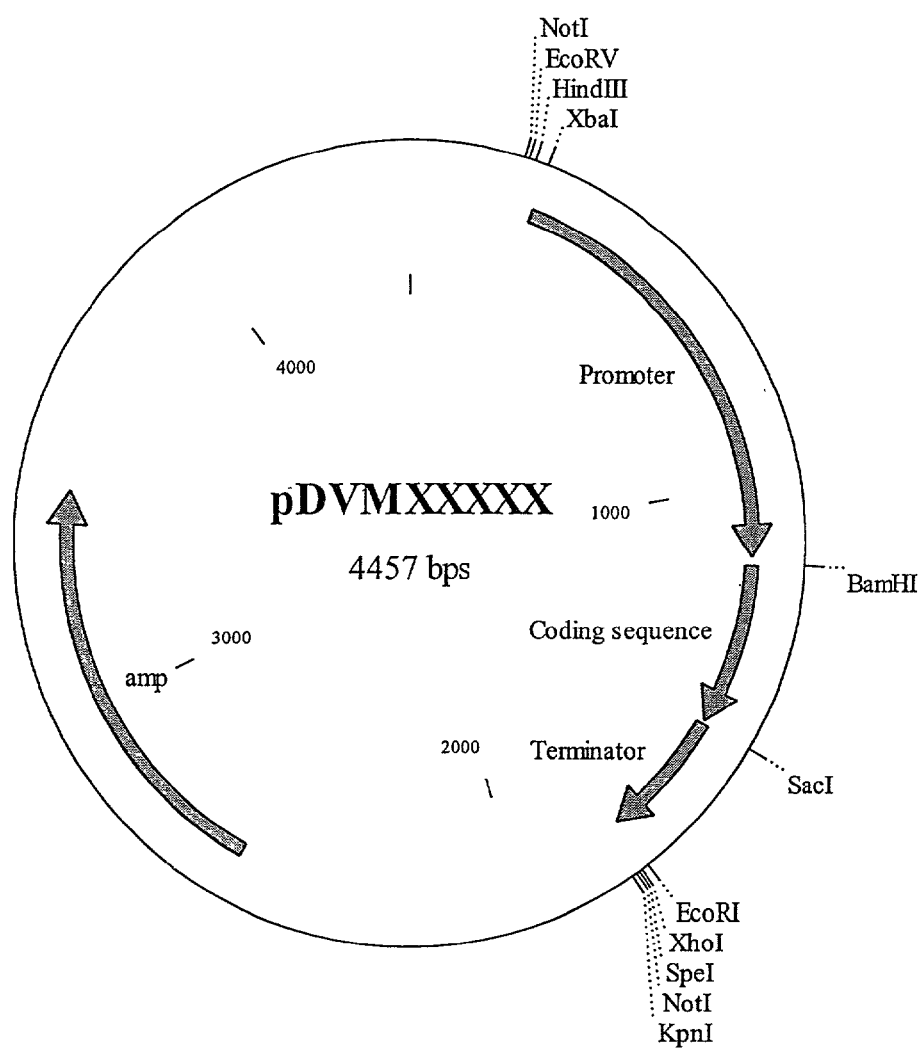
FIG. 11 shows the cloning vector pDE4.

Production of Constructs Comprising the Maize Ribosome Inactivating Protein for Assessment in Transient Protoplast Assays Constructs containing the cauliflower mosaic virus 35S constitutive promoter linked to a coding sequence derived from the maize ribosome inactivating protein and a Nos terminator sequence were produced in a pDE4 derived vector (Denecke et al, 1990) (see FIG. 11) suitable for use in a transient expression protoplast system. The following constructs were made and schematics are shown in FIG. 5:

1. pDE4 35S/Pro RIP
2. pDE4 35S/RIP P ("mature" RIP)
3. pDE4 35S/RIP α
4. pDE4 35S/RIP β

Transient Assay of RIP Constructs in Tobacco Protoplasts

In this assay ribosome inactivating protein-mediated ribosome inactivation was detected by way of assessing GUS protein synthesis. Protoplasts were prepared from leaves of in vitro-maintained tobacco plants and were electroporated with the RIP constructs. The protein translation efficiency of ribosomes in the tobacco protoplasts was evaluated with a GUS reporter gene in a pDE4 construct under the control of a CaMV 35S promoter. A GUS pDE4 construct was co-electroporated with each RIP construct. In order to obtain values for the optimum levels of GUS protein synthesis in protoplasts in competition with a second protein, a GUS-positive control was used, wherein a non-toxic BiP protein construct, pDE800 (Leborgna-Castel et al, 1999) was co-electroporated into tobacco protoplasts together with the GUS pDE4 construct. A GUS-negative control was also used, wherein an empty pDE4 vector was electroporated into tobacco protoplasts together with the non-toxic BiP chaperone protein construct.

(i) Mature Maize RIP-P.

Maize RIP-P constructs were co-electroporated with the GUS construct into tobacco protoplasts. The effect of maize RIP activity on ribosomes was assayed by measuring the levels of GUS activity after 24 hours of expression (FIG. 1). The dosage effect of the construct was assayed by electroporating different quantities (0.02 μg to 20 μg) of the maize RIP-P construct (FIG. 2).

The results demonstrate that mature maize RIP-P protein inactivates tobacco ribosomes efficiently. Consequently only basal levels of GUS activity are observed in comparison with the GUS positive control.

The efficiency of ribosome inactivation depended on the amount of input DNA electroporated into the protoplasts. Higher amounts of RIP DNA (20 μg) induced ribosome inactivation rapidly and only basal levels of GUS activity was observed. Lower amounts of input DNA (0.02 μg) resulted in much greater residual GUS activity, possibly due to the longer time taken for the RIP to reach critical protein concentrations and completely inactivate the ribosomes.

(ii) Maize RIP-P Activity on Different Ribosomes of the Cell:

An experiment was conducted to test whether the maize RIP-P depurinates both the ribosomes on the Endoplasmic Reticulum (ER) and those in cytosol. As an example of a protein synthesised on the ER, α-Amylase protein possesses an N-terminal signal sequence and the protein is secreted via the ER. An α-Amylase construct was co-electroporated into protoplasts along with the RIP-P construct, and a GUS construct was also used for comparison. After 24 hours expression, an amylase assay was performed (FIG. 3).

The results indicated no significant difference between the effect of RIP-P on the α-Amylase and on the GUS activities. The mature maize RIP-P inactivated all ribosomes irrespective of their cellular location. The results of these assays with maize RIP-P indicate that the enzyme is highly effective to induce complete ribosome inactivation and subsequent cell attenuation or cell death.

(iii) The Separate Maize RIP Domains

Maize RIPα and RIPβ polypeptide regions were also expressed either individually or in combination in tobacco protoplasts (FIG. 4).

Expression of RIPα protein alone surprisingly resulted in a significant reduction in the GUS activity. In contrast, expression of RIPβ protein alone was found to be inactive. On the basis of structural predictions, RIPα contains the RNA recognition motif and ribosome binding domain regions, but not the critical catalytic residue site. RIPα protein may be preventing protein translation by binding to ribosomes and preventing the protein translation. This would imply that RIPα is adopting a correctly folded conformation and is capable of specific molecular recognition. RIPβ contains the active site residue necessary for ribosome depurination and might not be expected to be capable of interacting with the ribosome.

Expression of both RIPα and RIPβ simultaneously in protoplasts resulted in further reduction of GUS activities in comparison with RIPα and RIPβ proteins alone. This implies that the two peptides are able to interact and facilitate ribosome depurination.

Isolation of a Promoter that is Induced at and/or Adjacent to a Target Site

A method is hereby presented for the isolation of a promoter, which method is by way of an example. Alternative methods for the isolation of a suitable promoter for use in the present invention will be readily available to the skilled person, some of which methods are referenced above.

A Method for the Isolation of the KNT1 Promoter is as Follows: Growth and Infection of Tobacco Plants Seed of C319 tobacco was germinated on Fisons F1 compost under conditions as follows: light intensity of 4500 to 5000 lux; 16 hr day/8 hr night; temperature 20–25° C. After c. 3 weeks seedlings were gently washed in tap water to remove soil and transferred to pouches (Northrup-King), 2 plants per pouch, and grown for a further week in a Conviron at 25° C. with lighting as above. Roots were lifted from the back of the pouch and supported with Whatman GF/A glass fibre paper at their tips. Three-day-old nematodes (*M.javanica*) were then delivered to the tips of these roots in 10 μl (50 nematodes) aliquots and a second piece of GF/A paper was placed on top to fully encapsulate the root tip. Following 24 hours post infection, the GF/A paper was removed to ensure synchronous infection. Following 3 days post infection the root knots were dissected out (leaving healthy root and root tip tissue behind) and frozen immediately in liquid nitrogen. Approximately 0.5–1.0 g of infected root tissue was harvested from 80 inoculated plants.

Staining for Visualisation of Nematodes in Infected Roots

The quality of infection was established by determining the number of nematodes infecting per root tip. Roots were harvested from 3 day post infected plants and immersed for 90 seconds in lactophenol containing 0.1% Cotton Blue at 95° C. Following a 5 second rinse in water, the roots were placed in lactophenol at room temperature (RT) for 3–4 days to clear. Stained nematodes were visualised using light microscopy.

RNA Isolation From Healthy and Infected Root Tissue

Root tissue was ground to a fine powder in a liquid nitrogen chilled pestle and mortar. Approximate 100 mg aliquots were then transferred to similarly chilled microfuge tubes and 300 µl of hot phenol extraction buffer (50% phenol, 50% extraction buffer: 0.1M lithium chloride, 0.1M Tris-HCl pH 8.0 (RT), 10 mM EDTA, 1% SDS) added, and incubated at 80° C. for 5 minutes. An equal volume of chloroform was then added and the homogenate microfuged for 15 minutes at 4° C. The aqueous phase was then extracted with 600 µl of phenol/chloroform and microfuged as above. The aqueous phase was again removed and the RNA precipitated with an equal volume of lithium chloride at 4° C. overnight. The precipitate was pelleted by microfugation for 15 minutes at RT and washed in 70% ethanol. The pellet was lyophilised, resuspended in DEPC-treated water and assayed using a spectrophotometer. RNA quality was assessed by denaturing gel electrophoresis. (Adapted from Shirzadegan et al, 1991).

Substractive Cloning of Infection Specific cDNAs

Poly(A)$^+$ RNA (mRNA) was isolated from 200 µg total RNA samples from healthy and infected C319 root tissue using magnetic oligo dT Dynabeads according to the manufacturer's instructions. First strand cDNA synthesis was performed in situ on the Dynabead-bound poly(A)$^+$ fraction from healthy tissue to provide Driver DNA. First and second strand synthesis was performed in situ on the Dynabead-bound poly(A)$^+$ fraction from the infected tissue to provide Target DNA. All cDNA reactions were carried out using a cDNA synthesis kit according to the manufacturer's instructions (Pharmacia). Three oligonucleotides, SUB 21 (5' CTCTTGCTTGAATTCGGACTA 3') (SEQ. ID. No.: 15), SUB25 (5' TAGTCCGAATTCAAGCAAGAGCACA 3') (SEQ. ID. No.: 16) (sequences from Duguid & Dinauer, 1990) and LDT15 (5' GACAGAAGCGGATCCd(T)$_{15}$ 3') (SEQ. ID. No.: 17) (O'Reilly, 1991) were kinased with T4 polynucleotide kinase according to Maniatis et al (1982). SUB21 and SUB25 were then annealed to form a linker which was then ligated to the Target DNA with T4 DNA ligase according to King & Blakesley (1986). Subsequently the beads carrying the Target DNA were washed extensively with TE and the second strand of the cDNA eluted at 95° C. in 5×SSC.

The RNA bound to the Dynabead-bound Drive DNA was removed by heat and the eluted Target DNA hybridised to the Driver DNA at 55° C. in 5×SSC for 5 hours. Non-hybridising Target DNA was separated from the bead-bound Driver DNA at room temperature (RT) as per the manufacturer's instructions, following which, hybridising Target DNA was similarly separated from the bead-bound Driver DNA at 95° C. The RT eluted Target DNA was then added back to the Driver DNA and the hybridisation repeated. This process was repeated until the amount of Target hybridising to the Driver no longer exceeded the amount that did not hybridise. DNA concentrations were established using DNA Dipstick (Invitrogen) in accordance with the manufacturer's instructions.

Aliquots of the final RT-eluted fraction were used in PCR amplification (Eckert and Kunkel, 1990) to generate double-stranded cDNA for cloning into a plasmid vector. Amplification of the target DNA was achieved using primers SUB21 (SEQ. ID. No.: 15) and LDT15 (SEQ. ID. No.: 17) according to the conditions described by Frohman et al, 1988. The PCR products were then ligated into SmaI digested pBluescript vector according to King and Blakesley (1986).

Screening of the Subtractive Library by Reverse Northern Analysis

Recombinants were identified by colony PCR (Gussow and Clackson, 1989). The amplified inserts were Southern blotted in triplicate onto Pall Biodyne membranes and prescribed by the manufacturer. Pre-hybridisation and hybridisation were both carried out at 42° C. in 5×SSPE, 0.05% BLOTTO, 50% formamide. Membranes were hybridised separately to cDNA probes (see below) from healthy and infected tissue and to a probe comprising amplified Target DNA from the final subtraction. Clones showing a hybridisation signal to the infected cDNA probe only, or showing a hybridisation signal to the subtracted probe only were selected for further analysis.

cDNA Probe Generation

Samples of 10 µg total RNA from healthy and infected tissue were treated with 2.5 units DNaseI at 37° C. for 15 minutes. The DNaseI was then denatured at 95° C. for 10 minutes before cDNA synthesis was performed using the manufacturer's protocol (Pharmacia). The RNA was then removed by the presence of 0.4 M sodium hydroxide for 10 minutes at RT and the cDNA purified through a spun Sephacryl 400HR column. Yield and concentration was determined using DNA Dipsticks (Invitrogen). The cDNA was labelled, using c. 35 ng/probe using the standard Pharmacia oligolabelling protocol.

Northern Blotting

To determine the expression profile of the clones selected from Reverse Northerns, they were used as probes in Northern analysis of either total or poly(A)$^+$ RNA from healthy and infected roots, stems, leaves, and flowers. Total RNA blots comprised 25 µg RNA per lane, whilst poly(A)$^+$ RNA blots comprised 0.5–1.0 µg RNA per lane. The RNA was electrophoresed on formaldehyde gels and blotted onto Pall Biodyne B membrane as described by Fourney et al (1988). Probes were labelled and hybridised as above.

Southern Blotting

To determine whether selected cDNAs were of plant or nematode origin, tobacco C319 and *M.javanica* DNA were prepared as described by Gawel and Jarret (1991). Southern blots were prepared comprising 10 µg EcoRI and HindIII digested DNA per lane. The blots were hybridised to oligo-labelled probes as described above.

In Situ Hybridisation

To determine the locality of expression of the cDNAs of interest at the feeding site, in situ hybridisations were performed. Tissue from infected and healthy roots were embedded in wax, sectioned, and hybridised to the probes as described by Jackson (1991).

Isolation of 5' Termini of mRNAs

The 5' termini of the RNAs of interest were determined by using 5' RACE as described by Frohman et al (1988).

Isolation of Promoter Regions

The promoter regions of the genes of interest were isolated by vector-ligated PCR. 100 ng samples of restriction endonuclease digested C319 genomic DNA were ligated for 4 hours at RT (King and Blakesley), 1986) with 100 ng samples of pBluescript (digested with a restriction endonuclease producing compatible termini). Typically enzymes used were EcoRI, BamHI, HindIII, BglII, XhoI, ClaI, SalI, KpnI, PstI, and SstI. PCR was then performed on the ligations using a vector primer such as the −40 Sequencing primer and a primer complementary to the 5' terminus of the mRNA. The PCR products were then cloned and sequenced. If necessary the process was repeated with a new primer complementary to the 5' terminus of the promoter fragment to ensure that the control sequences of the promoters were isolated.

Using the procedures described above, a gene, KNT1, was identified and isolated from tobacco plants. A KNT1 promoter fragment of approximately 0.8 Kbp in length from the transcription start site, was isolated and inserted into the GUS reporter vector, pBI101 (Jefferson et al, 1987). The resulting construct, pBIN05101, was used to transform tobacco plants. Upon infection with *M.javanica*, strong GUS expression was observed in the nematode feeding site.

The KNT1 gene was shown to have homologues in species of plant other than tobacco. These include, but are not limited to *Solanum tuberosum, Lycopersicon esculentum* and *Beta vulgaris*. The KNT1 gene is also induced by both root knot and cyst nematode species.

The construct pBIN05101 was deposited by Advanced Technologies (Cambridge) Limited of 210 Cambridge Science Park, Cambridge CB4 0WA, England under the Budapest Treaty on the International Recognition of the Deposit of Micro-organisms for the purposes of Patent Procedure at the National Collections of Industrial, Food and Marine Bacteria (NCIMB), 23 St. Machar Street, Aberdeen, Scotland on 20 Mar. 1997 under accession number NCIMP 40870. The vector contains the left and right borders of *Agrobacterium tumefaciens* C58 strain T-DNA. Between the borders are a multiple cloning site and a kanamycin resistance gene under the control of a plant promoter (Nos). External to the borders the vector contains a bacterial kanamycin resistance gene. The insert in the vector consists of the KNT1 promoter—glucuronidase coding sequence—nos terminator.

Production of Constructs for Plant Transformation Studies, Which Constructs Comprise the Maize Ribosome Inactivating Protein and Promoters Which are Induced at and/or Adjacent to a Nematode Feeding Site Constructs comprising the KNT1 nematode-responsive promoter linked to a coding sequence of the maize ribosome inactivating protein and a Nos terminator in a pATC derived plant transformation vector (FIG. 10) were used in the transformation studies. These were designed to study the effectiveness of RIP constructs to induce cell death in the assembled in the pDVM vector and then the transgene cassettes excised with restriction endonuclease NotI and cloned into the binary vector pATC. The constructs were introduced into *Agrobacterium tumefaciens* LBA4404 by electroporation. The constructs produced were as follows:

1. pATCKNT1/Pro RIP
2. pATCKNT1/RIP-P
3. pATCKNT1/RIP α
4. pATCKNT1/RIP β

A final construct was prepared comprising both the RIP α and the RIP β coding regions under two separate nematode-responsive promoters (FIG. 5). The second promoter used was designated KNT2 (see SEQ. ID. No.: 18). This construct was named:

pATC KNT2/RIP α KNT1/RIP β

The KNT1 promoter expresses in the feeding site cells, root tips and to a much lesser extent in other meristems. The KNT2 promoter expresses in root body and feeding site cells (but not root tips). There is thus overlap expression at the feeding site cells causing enhanced specific plant cytotoxicity where the α and β domains are jointly expressed.

Constructs for use in the other embodiments of this invention are similarly prepared with suitable targeting promoters for the alternative appropriate embodiment.

Production of Transgenic Plants Containing Maize RIP Constructs Under the Control of Nematode-Inducible Promoters.

All of the constructs above (see FIG. 5) were introduced into potato cv. Hermes and tobacco cv. K326, by leaf disc co-cultivation using *Agrobacterium tumefaciens* LBA4404 (Horsch et al, 1985).

Transgenic plants of potato and tobacco were generated, and greenhouse nematode resistance trials were conducted.

Resistance Screens Using Tobacco Plants Infected with *Meloidogyne javanica*

Transgenic and control tobacco plantlets were planted in a randomised blind experimental design into rootrainers fine potting compost without fertiliser and the larger leaves trimmed by half. The plants were covered with polythene to maintain high humidity whilst weaning. Gradually holes were slit in the polythene to decrease humidity before weaning was completed. One week after weaning, the small plants were infected with 200 hatched J2 *Meloidogyne javanica* nematodes. Watering with liquid feed thereafter was only done once the soil had dried sufficiently to cause the leaves to start wilting. The rootrainers were placed in trays on heated matting to maintain the soil temperature between 25–30° C. The leaves were trimmed back once a week in order to even out growth and prevent the growing points becoming covered with larger leaves due to density of planting.

The plants were harvested for scoring approximately 8 weeks after infection. Typically, the roots were washed and scored for root growth, level of gall formation and size of galls.

Resistance Screens Using Potato Plants Infected with *Globodera pallida* Pathovar ⅔

Primary resistance trials of transgenic plants were conducted in blind randomised trials on batches of 20 to 25 transgenic lines with at least ten replicates of 2 or more control lines. Rootrainers or containers were filled with a mixture of 50:50 loam and sand. 12 liters of loam and sand is moistened with 1250 mls of water to give a 40% water content. 3 cysts were placed onto the roots of each plantlet which was then inserted into a hole in the compost and the compost gently closed around the roots. The plants were weaned and thereafter, only watered once weekly with liquid feed or when the soil had dried sufficiently. Once the plants reached approx. 10 cm in height, the tips were trimmed off to even out growth.

The plants were grown for approximately three months to permit the cysts to mature. The plants were then allowed to ary out for another month. Cysts were recovered from the plants by washing the soil and roots vigorously in a beaker of 250 ml water. The soil was permitted to settle for a few minutes and the supernatant poured into a large filter funnel with a 32 cm diameter Whatman No. 1 filter paper disc. The supernatant was left to stand in the funnel for a minute and then the centre of the solution surface was touched with a drop of Hederol detergent to displace the material on the surface meniscus of the solution to the side of the filter. The base of the filter was then pierced to remove the remainder of the solution. The filter disc was removed and the number of cysts adhering to it was counted.

Plants were regarded as showing signs of resistance if they are infected with fewer cysts than susceptible control lines.

Scoring for Infection of Tobacco and Potato With Nematodes by Staining

Tobacco plants from tissue culture or seedlings were planted and grown as described above with the following modification. Plants were infected with 1000 hatched J2 *Meloidogyne javanica* nematodes. Potato plants were infected with *Globodera pallida* as described above.

One month after infection, cuttings were taken from the plants. The roots were washed clean of soil and bleached for 4 minutes in 1% sodium hypochlorite. The bleach was removed by rinsing with water and then soaking in a large volume of water over 15 minutes with occasional agitation. The roots were then placed in 10 to 15 ml of a 1:500 dilution of acid fuchsin stock solution in 5% acetic acid. (Acid fuchsin stock was prepared according to "Introduction to Plant Nematology" by V. H. Dropkin, ISBN 0-471-85268-6. Dissolve 0.35 g acid fuchsin in 100 mls of 1:3 glacial acetic acid to distilled water). The samples in stain were placed in a boiling water bath for 4 minutes and transferred to 37° C. for four hours. The stain was decanted and the samples are cleared by adding acidified glycerol and incubating at 37° C. overnight.

The cleared roots with stained nematodes were then mounted in petri-dishes (the sample was placed on the inner side of the lid of a petri dish and the base of the petri dish is used to spread out and compress the sample for easier viewing under the microscope).

The samples were viewed at 20 to 100×magnification and nematodes were scored in several ways. Root knot nematodes were categorised into three groups: a) vermiform nematodes, b) saccate nematodes that are not providing eggs and c) saccate nematodes producing eggs. The diameters of the essentially saccate nematodes were measured using an eyepiece graticule. Cyst nematodes were also categorised into three groups: a) vermiform nematodes, b) fat vermiform nematodes that are not producing eggs and c) globose nematodes producing eggs. The diameters of the essentially globose nematodes were measured using an eyepiece graticule.

Resistance effects were measured in terms of absolute numbers of nematodes in root systems, in terms of the proportion of nematodes reaching maturity and producing eggs and in terms of the size of the nematodes.

A number of resistance lines of tobacco and potato were identified expressing maize RIP as a single effector component as well as a two-component system.

Pot Trial of Selected Maize RIP Potato Lines

Chitted tubers of selected potato cv Hermes lines were replicated and used in a standard potato cyst nematode resistance trial with *G.pallida* race ⅔ to which only partial resistance is available. The potatoes comprised four lines transformed with the processed maize RIP-P and four lines transformed with the two component RIPα/RIPβ construct. The trial included untransformed Hermes and Prairie as both stock tubers (control) and material that has been through the same tissue culture procedure as the transgenic plants (control ncc). In addition, the trial included the untransformed control varieties Desiree and Maris Piper (both PCN-susceptible), and Sante (partial resistance to PCN race ⅔, the best commercially available line.

Table 1 gives a summary of the results expressed as a percentage susceptibility of the transgenic lines relative to non-resistance controls.

TABLE 1

| Construct | Cultivar | Line | Percentage Susceptibility |
|---|---|---|---|
| RIP P | Hermes | 1 | 143 |
| RIP P | Hermes | 10 | 72 |
| RIP P | Hermes | 13 | 45** |
| RIP P | Hermes | 15 | 63 |
| RIPα/RIPβ | Hermes | 9 | 44** |
| RIPα/RIPβ | Hermes | 11 | 65 |
| RIPα/RIPβ | Hermes | 14 | 103 |
| RIPα/RIPβ | Hermes | 15 | 88 |
| NCC Control | Hermes | | 90 |
| Control | Hermes | | 139 |
| NCC Control | Prairie | | 115 |
| Control | Prairie | | 93 |
| Control | Desiree | | 94 |
| Control | Maris Piper | | 62 |
| Control | Sante | | 21 |

There was a large degree of variation in PCN cyst counts both between the controls and between individual replicates, which can be attributed to environmental factors. However, one processed maize RIP line (RIP-P) and one two-component maize RIP line showed a significant reduction in susceptibility relative to the control lines. These are marked by ** in Table 1. In the two-component system it is surprising to note that some plants remain viable, despite expression of α or β RIP at the non-overlapping sites.

Analysis of Nematodes in Transgenic Tobacco Lines Expressing Maize RIP

Progeny from transgenic tobacco lines transformed with the processed maize RIP-P or the two-component maize RIP construct were infected with root knot nematodes. One month after infection, roots from the infected plants were treated with Acid Fuchsin to stain the nematodes in situ. Galls and stained nematodes were counted and assigned to the following four categories; empty galls, vermiform juveniles, spherical adults, egg-laying adults (FIG. 9).

Whilst there was no significant difference in the total number of nematodes and galls per line between the transgenic lines and the controls, three transgenic lines, D, G and K, showed fewer egg-laying adults.

In order to determine whether maize RIP lines reduce the growth of nematodes in plants the size of adult nematodes was measured as described above.

Non-egg-laying adult nematodes were significantly smaller for-lines D, G and K compared to those on the control plants (FIG. 6). However, the sizes of egg-laying nematodes showed much smaller differences (FIG. 7), indicating that egg-laying appears to occur only when the nematodes have reached a minimum size (of 32 to 36 graticule units). Expression of the RIP appears to slow down the growth of the nematode, resulting in delay in reaching egg-laying size (FIG. 8).

In contrast, those lines which did not show any reduction in the number of infecting nematodes or in the number of egg-laying females did not show the decrease in adult female size as observed with lines D, G and K.

These results therefore indicate that the maize RIP and two-component maize RIP constructs affect the development of the root knot nematodes.

For use in other aspects of the invention the appropriate promoter is utilised with a maize ribosome inactivating protein or part thereof in operable linkage in accordance with the processes described in this exemplified aspect.

Male Sterility Induced in Pollen by Expression of a Ribosomal Inactivating Protein (RIP)

Constructs

Figure 13:
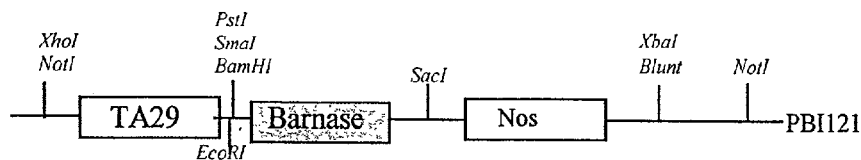
FIG. 13 shows the construct used to produce male sterility.
Figure 13:
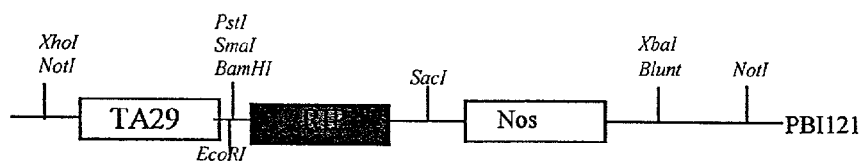
Figure 13:
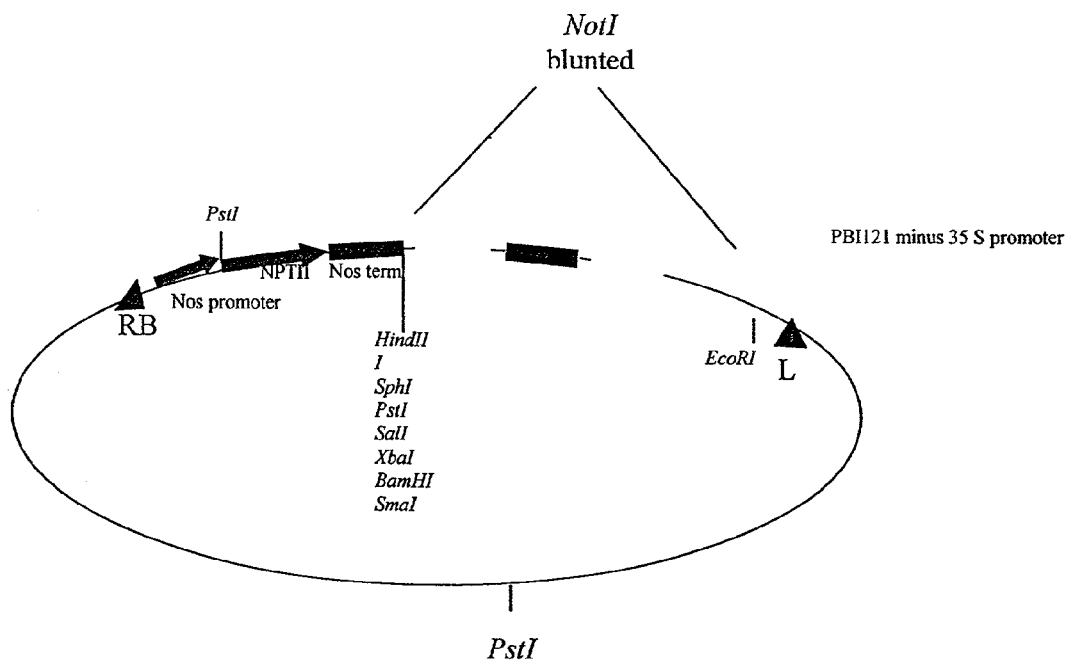

The sequence of barnase from *Bacillus amyloliquefaciens* (Hartley R. W. 1998) and a ribosomal inactivating protein (RIP-P; SEQ.ID.No.: 2) from maize kernels (Bass et al 1995) were each inserted in separate constructs behind a tapetal-specific promoter (TA29, Mariani, C., 1989) from *Nicotiana tabacum*. The constructs were produced (FIG. 13) and transformed using the plant vector pBI121 (minus the 35S CaMV promoter). Constructs were transformed into the *Solanum tuberosum* spp *tuberosum* cv Desiree to allow direct comparison with normal phenotypic Desiree.

Transformation and Regeneration of Transgenic Plants

This above cassette was cloned into the binary vector pBI121 as a Not I fragment. The final construct was introduced into competent *Agrobacterium fumefaciens* LBA4404 by electroporation as described by Shen W. et al, 1989.

Subsequently leaf discs of *Solanum tuberosum tuberosum* cv. Déirée were transformed as described by a standard protocol (Dietze J. et al 1995). Transgenic plants were rooted in liquid MS (Murashige, T. and Skroog, F., 1962) supplemented with 0.1 mg $1^{-1}$ NAA before transfer to soil.

Regenerated plants were transplanted into pots of 50:50 sand:loam mix. Plants of each cultivar were grown in a containment glasshouse at 18±2° C. under a 14 h day length with watering as required. Non-transgenic lines were established in tissue culture from stems of plants grown in a glasshouse. Plants generated from this source were transplanted to the glasshouses concurrently with transgenic lines.

Transgenic and control lines were screened for viable pollen using both a pollen tube germination bioassay and their ability to take up fluorescein diacetate. Lines selected as showing a loss of viable pollens plus control plants were subsequently used in hand-crossing experiments to confirm the ability or inability of their pollen to cross-fertilise to the stigma of another potato plant.

Pollen Tube Formation

Pollen germination was studied using the protocol of Krishnakumar and Oppenheimer (1999).

Glass slides were coated with molten pollen germination medium. This is solution at pH 6 of 1 mM $CaCl_2$, 1 mM Ca $(NO_3)_2$, 1 mM $MgSO_4$, 0.01% boric acid, 18% sucrose and 0.5% agarose. An anther was removed from the test plant and its pollen knocked from it onto the slide. The latter was then left for 18 hr in chamber with about 100% relative humidity in an incubator at 22–25° C. in the dark. A coverslip is mounted on the slide and proportion of grains with germination tubes counted by examining pollen grains under bright field illumination. FIG. 14 shows pollen tube formation for wild-type pollen but their absence from the abnormal pollen of one of the RIP-P lines that were selected as showing male sterility.

Fluorescein Diacetate (FDA) Staining of Viable Pollen

The procedure uses a stock solution of fluorescein diacetate made up at 2 mg/ml in acetone. Before use it was diluted 1000 fold in a 20% sucrose in distilled water that had previously been filter sterilised. Anthers were removed individually from a potato flower with forceps and dabbed onto a glass slide to collect pollen grains. The diluted FDA solution was added and a coverslip mounted on the slide. The preparation was examined immediately under a microscope (Leica DMR) with epi-illumination and appropriate filters for examination of fluorescent emissions by fluorescein. Images were recorded using a camera attachment (Olympus OM4) and reversal film (Kodak Elite 100 ASA). FIG. 15 shows an example of wild-type pollen in bright field illumination. In comparison, the transgenic lines expressing SEQ. ID. No.: 2 or barnase provided pollen that was shrivelled and did not form pollen tubes. This indicated a lack of vaiability for the pollen from the transgenic lines.

As a result of both pollen tube germination assays and FDA uptake a total of 8 of 37 RIP-P lines that were assayed were selected as having very low pollen viability. A total of 2 of 21 barnase lines were also shown to lack viable pollen. The data for each of these lines plus an example for each constructs of a line rejected as not adequately male sterile are given in Table 2. Some control lines are also included.

TABLE 2

| Construct | Pollen grains examined | Pollen tubes formed | Pollen grains examined | FDA taken up |
|---|---|---|---|---|
| Lines selected as male sterile | | | | |
| RIP 04 | 10 | 0 | 50 | 0 |
| RIP 11 | 100 | 1 | 100 | 1 |
| RIP 21 | 100 | 1 | 100 | 0 |
| RIP 22 | 100 | 1 | 300 | 1 |
| RIP 33 | 100 | 0 | 100 | 1 |
| RIP 41 | 100 | 1 | 100 | 1 |
| RIP 44 | 100 | 0 | 100 | 0 |
| RIP 48 | 500 | 1 | 500 | 0 |
| Total | 1110 | 5 | 1350 | 4 |
| Bar 12 | 50 | 0 | 200 | 0 |
| Bar 38 | 100 | 1 | 300 | 1 |
| Total | 150 | 1 | 500 | 1 |
| Examples of lines not selected as adequately male sterile | | | | |
| RIP 32 | 100 | 3 | 100 | 5 |
| Bar 7 | 10 | 4 | 10 | 8 |
| Total Controls | 110 | 7 | 110 | 13 |
| Maria Huanca | 10 | 4 | 100 | 20 |
| Desiree | na | na | 100 | 90 |
| Total | 10 | 4 | 200 | 110 |

Eight RIP and two barnase expressing, transgenic lines were selected as male sterile from pollen tube germination bioassays and by a low incidence of uptake of FDA by pollen grains. For comparison, two transgenic lines not showing a high level of non-viable pollen and untransformed wild-type control potato cultivars are shown (na=not assayed).

The difference in frequency of pollen tube germination or FDA uptake for the positive RIP and barnase lines was statistically different from that for controls ($\chi 2$ test, P<0.001 in both cases).

Manual Pollination of Potato

This procedure was used to check that both a particular RIP (SEQ. ID. No.: 2) and a barnase line assessed as male sterile by pollen tube germination and FDA uptake failed to fertilise a stigma of a potato flower receiving the pollen. A range of control cultivars was also chosen for this work. The cultvars Revolution and Waycha are forms of *Solanum tuberosum* spp *andigena*. They were chosen as cv Waycha produces berries profusely while Revolution is a male sterile and so no berries are formed unless pollen is donated to it. The control experiments establish that manual pollination is often successful with a viable pollen source.

The *Solanum tuberosum* spp *tuberosum* cultivar Desiree was also used in the work. It produces berries profusely and is a cultivar for which true potato seed commonly forms. Given its normal ability to produce berries profusely it represents a suitable cultivar to determine the loss of this ability using one of the RIP genes that is subject of this invention. The efficacy of this transgene in preventing fertilisation was compared with that obtained using a barnase.

When a flower formed, it was prepared for forced hand crossing. If it was to be a recipient of pollen, its petals and then anthers were cut away so that the stigma protruded. If the flower was to be a pollen donor, the petals and stigma were cut away. In this case a single anther was taken with forceps and tapped against the surface of a black tile so the pollen deposition could be checked by eye. The pollen source was wiped across the stigma of the receipients or donors of pollen. All unused flowers were cut from the plant. When a stigma was successfully fertilised, the flower did not drop and it began to swell to form a berry. If fertilisation failed, the stigma fell from the plant within a week and no berry formed. The presence of berries was a reliable preliminary indicator that fertilisation had occurred. Preliminary experiments established that berries contained seeds but their number per berry was not routinely counted.

The results shown in Table 3 confirm that pollen of line RIP line 33 and barnase line 12 selected as male sterile from pollen tube termination bioassays and lack of FDA uptake by pollen grains did fail to fertilise the stigma of potato.

TABLE 3

| Construct | Pollen recipient | Pollen donor | Number of hand crosses attempted | Number of stigma forming berries |
|---|---|---|---|---|
| None | Revolution | Waycha | 11 | 4 |
| None | Waycha | Waycha | 11 | 5 |
| Bar 12 | Desiree | Desiree | 10 | 0 |
| RIP 33 | Desiree | Desiree | 5 | 0 |

Table 3 shows a summary of hand crosses to individual stigma for different cultivars as recipients or donors of pollen and the number of berries that subsequently resulted. The crosses with transgenic Desiree were to confirm the conclusion of a high level of male sterility for two lines identified as male sterile in pollen tube germination bioassays and by lack of FDA uptake by pollen grains.

REFERENCES

Bass H. W., O'Brian, G. R. and Boston, R. S. (1995) Plant Physiol. 107, 661–662

Deneck J., Betterman J. and Deblaere R. (1990) The Plant Cell 51–59

Dietze J., Blass A., Willmitzer L. (1995) *Agrobacterium*-mediated transformation of potato (*Solanum tuberosum*). In: Potryka I. S. and Spangenburg G. (eds). Gene transfer to plants. Springer Lab. manual pp 24–30.

Duguid J. R. and Dinauer M. C. (1990) Nucleic Acids Research 18(9) 2889–2792

Eckert K. A. and Kunkel T. A. (1990) Nucleic Acids Research 18(13) 3737–3744

Fourney R. M., Miyakoshi J., Day III R. S. and Paterson M. C. (1988) Focus 10(1) 5–7

Frohman M. A., Dush M. K. and Martin G. R. (1988) Proceedings of the Natl. Acad. Sci. USA 85 8998–9002

Gawel N. J. and Jarret R. L. (1991) Plant Molec. Biol. Reporter. 9(3) 262–266

Gussow D. and Clackson T. (1989) Nucleic Acids Research 17 4000–4008

Hartley H. W. (1998) J. Mol. Biol., 202, 913–915

Horsch R. B., Fry J. E., Hoffman N. L., Eicholtz D., Rogers S. G. and Fraey R. T. (1985) Science 227 1229–1231

Jackson D. (1991) Molecular Plant Pathology: A Practical Approach. IRL Press, Oxford.

King P. V. and Blakesley R. W. (1986) Focus 8(1) 1–3

Krishnakumar and Oppenheimer (1999) Development, 126, 3079–3088

Leborgna-Castel N., Jelitto-Van Droven E. P. W. M., Crofts A. J. and Denecke J. (1999) The Plant Cell 11 459–469

Lemmetyinen, J., Pennanen, T. Lannengpaa M. and Sopanen T. (2001) Molecular Breeding, 7 341–350

Maniatis T., Fritsch E. F. and Sambrook J. (1982) Molecular Cloning; A Laboratory Manual. N.Y. Cold Spring Harbour Laboratory.

Mariana et al (1990) Nature 347 737–741

Mariana, C., Leemans, J., De Gref, W. and de Beuckeleer, M. (1989) EP0 344029

Murashiga, R. and Skroog F. (1962) Physiol. Plant, 15, 473

O'Reilly D., Thomas C. J. R. and Coutts R. H. A. (1991) J. Gen. Virology 17 1–7

Perry S. E., Nicholas K. W. and Fernandez D. E. (1996) the Plant Cell 8 1977–1989

Samach A., Kohlmai S. E., Motte P., Datla R. and Haughn G. W. (1997) The Plant Cell 9 559–570

Shen, W. and Forde, B. G., Nucleic Acids Research, 17, 83–85

Shirzadegan M., Christie P. and Seemann J. R. (1991) Nucleic Acids Research 19 (21) 6055

Sieburth L. E. and Meyerowitz E. M. (1997) The Plant Cell 9 355–365

Stirpe and Barbiere (1986) FEBS Lett. 195, 1–8

Stirpe et al (1978) FEBS Lett. 85 65–67

Twell et al (1991) Molec. Gen. Genet. 217 240–245

The invention claimed is:

1. A method of producing a transgenic solanaceous plant, wherein cells of the solanaceous plant have within their genome a chimeric gene, the expression of which gene causes plant cell cytotoxicity by ribosome inactivation at a desired target site within the plant body, comprising (i) transforming plant cells with a chimeric gene comprising (a) a promoter, which promoter is induced at and/or adjacent to the target site, operably linked to (b) a nucleic acid molecule which binds to SEQ. ID. No.:2 in 0.5M $NaHPO_4$, 7% sodium dodecyl sulfate (SDS), 1 mm EDTA at 65° C. followed by washing in 0.1×SSC, 0.1% SDS at 68° C., wherein said nucleic acid molecule encodes a mature maize ribosome inactivating protein comprising an α domain and a β domain arranged contiguously and having type 3 ribosome inactivating activity; and (ii) the selective expression of the ribosome inactivating protein at the target site for induction of plant cell death at that target site.

2. A method of producing a transformed plant according to claim 1, wherein the nucleic acid molecule comprises SEQ. ID. No.: 2.

3. A method of producing a transformed plant according to claim 1, wherein said chimeric gene further comprises a 3' untranslated terminator sequence.

4. A method of producing a transformed plant according to claim 3, wherein said 3' untranslated terminator sequence is from plant, bacterial or viral genes.

5. A method of producing a transformed plant according to claim 3, wherein said 3' untranslated terminator sequence is selected from the group consisting of the pea rbcS E9 terminator sequence, the nos terminator sequence derived from the nopaline synthase gene of *Agrobacterium tumefaciens* and the 35S terminator sequence from cauliflower mosaic virus.

6. A method of producing a transformed plant according to claim 1, wherein said chimeric gene further comprises a transcriptional or translational enhancer sequence intracellular targeting sequences and introns, or nucleotide sequences operable to facilitate the transformation process and stable expression of said chimeric gene or combinations thereof.

7. A plant transformed with a chimeric gene according to the method of 1.

8. A plant cell comprising within its genome a chimeric gene, the expression of which gene causes plant cytotoxicity, said chimeric gene comprising (i) a promoter, which promoter is induced at and/or adjacent to a target site, operably linked to (ii) a nucleic acid molecule which binds to the nucleic acid molecule of SEQ ID NO.: 2 in 0.5M $NaHPO_4$, 7% sodium dodecyl sulfate (SDS), 1 mm EDTA at 65° C. followed by washing in 0.1×SSC, 0.1% SDS at 68° C., wherein said nucleic acid molecule encodes a mature maize ribosome inactivating protein comprising an α domain and a βdomain arranged contiguously and having type 3 ribosome inactivating activity.

9. A method of producing a transgenic solanaceous plant, comprising growing plants from a seed wherein said seeds have within their genome a chimeric gene, the expression of which gene causes plant cytotoxicity at a target site, said chimeric gene comprising (a) a promoter, which promoter is induced at and/or adjacent to the target site, operably linked to (b) a nucleic acid molecule which binds to SEQ. ID. No.:2 in 0.5M $NaHPO_4$, 7% sodium dodecyl sulfate (SDS), 1mm EDTA at 65° C. followed by washing in 0.1×SSC, 0.1% SDS at 68° C., wherein said nucleic acid molecule encodes a protein having type 3 ribosome inactivating activity wherein said nucleic acid molecule encodes a mature maize ribosome inactivating protein comprising an α domain and a β domain arranged contiguously and having type 3 ribosome inactivating activity.

10. A nucleic acid molecule comprising (a) a promoter, which promoter is induced at andlor adjacent to the target site, operably linked to (b) a nucleic acid molecule which binds to SEQ. ID. No.:2 in 0.5M $NaHPO_4$, 7% sodium dodecyl sulfate (SDS), 1 mm EDTA at 65° C. followed by washing in 0.1×SSC, 0.1% SDS at 68° C., wherein said nucleic acid molecule encodes a protein having type 3 ribosome inactivating activity wherein said nucleic acid molecule encodes a mature maize ribosome inactivating protein comprising an α domain and a β domain arranged contiguously and having type 3 ribosome inactivating activity.

11. A vector comprising the nucleic acid of claim 10.

* * * * *

SEQUENCE LISTING

<160> NUMBER OF SEQ ID NOS: 18

<210> SEQ ID NO 1
<211> LENGTH: 909
<212> TYPE: DNA
<213> ORGANISM: Zea mays
<220> FEATURE:
<221> NAME/KEY: misc_feature
<222> LOCATION: (1)..(48)
<223> OTHER INFORMATION: N-terminal Domain
<221> NAME/KEY: misc_feature
<222> LOCATION: (865)..(903)
<223> OTHER INFORMATION: C-terminal Domain
<221> NAME/KEY: misc_feature
<222> LOCATION: (484)..(558)
<223> OTHER INFORMATION: Central Domain
<221> NAME/KEY: mutation
<222> LOCATION: (226)..(231)
<223> OTHER INFORMATION: Sequence replacing removed SacI site
<221> NAME/KEY: misc_feature
<222> LOCATION: (1)..(3)
<223> OTHER INFORMATION: Initiation codon added via PCR primer
<221> NAME/KEY: misc_feature
<222> LOCATION: (904)..(909)
<223> OTHER INFORMATION: Stop codons added via PCR primer
<221> NAME/KEY: misc_feature
<222> LOCATION: (1)..(24)
<223> OTHER INFORMATION: Binding site for primer ProRIPBF
<221> NAME/KEY: misc_feature
<222> LOCATION: (205)..(249)
<223> OTHER INFORMATION: Binding site for primer RIPSDF
<221> NAME/KEY: misc_feature
<222> LOCATION: Complement((205)..(249))
<223> OTHER INFORMATION: Binding site for primer RIPSDR
<221> NAME/KEY: misc_feature
<222> LOCATION: Complement((880)..(909))
<223> OTHER INFORMATION: Binding site for primer ProRIPSR
<221> NAME/KEY: misc_feature
<222> LOCATION: (49)..(73)
<223> OTHER INFORMATION: Binding site for primer RIP1BF
<221> NAME/KEY: misc_feature
<222> LOCATION: Complement((837)..(864))
<223> OTHER INFORMATION: Binding site for primer RIP2SR
<221> NAME/KEY: misc_feature
<222> LOCATION: (463)..(579)
<223> OTHER INFORMATION: Binding site for primer RIPCDF spanning central
    domain
<221> NAME/KEY: misc_feature
<222> LOCATION: Complement((463)..(579))
<223> OTHER INFORMATION: Binding site for primer RIPCDR spanning central
    domain

<400> SEQUENCE: 1
atggccgaga taaccctaga gccgagtgat cttatggcgc aaacaaacaa agaatagtg      60 ccaaagttca ctgaaatctt ccccgtggag gacgcgaact accctttacag cgccttcatc    120 gcgtcggtcc ggaaagacgt gatcaaacac tgcaccgacc ataaagggat cttccagccc    180
gtgctgccac cggagaagaa ggtcccggag ctatggttct acacagaact gaaaactagg    240
accagctcca tcacgctcgc catacgcatg acaacctgt acctcgtggg cttcaggacc    300
ccgggcgggg tgtggtggga gttcggcaag gacggcgaca cccacctcct cggcgacaac    360
cccaggtggc tcggcttcgg cggcaggtac caggacctca tcgcaacaa gggtctggag    420 accgtcacca tggccgcgc cgaaatgacc agggccgtca cgacctggc gaagaagaag    480 aagatggcga cactggagga ggaggaggtg aagatgcaga tgcagatgcc ggaggccgct    540
gatctggcgg cggcggcagc ggctgaccca caggccgaca cgaagagcaa gctggtgaag    600
ctggtggtca tggtgtgcga ggggctgcgg ttcaacaccg tgtcccgcac ggtggacgcg    660

| gggttcaaca gccagcacgg ggtgaccttg accgtgacgc aggggaagca ggtgcagaag | 720 |
| tgggacagga tctccaaggc ggccttcgag tgggctgacc accccaccgc tgtgatcccc | 780 |
| gacatgcaga agcttggcat caaggataag aacgaagcag cgaggatcgt tgcgctcgtt | 840 |
| aagaatcaaa ctactgccgc tgccgctact gctgccagtg ctgacaacga cgacgacgag | 900 |
| gcctaataa | 909 |

```
<210> SEQ ID NO 2
<211> LENGTH: 750
<212> TYPE: DNA
<213> ORGANISM: Zea mays
<220> FEATURE:
<221> NAME/KEY: misc_feature
<222> LOCATION: (1)..(3)
<223> OTHER INFORMATION: Initiation codon added via PCR primer
<221> NAME/KEY: mutation
<222> LOCATION: (181)..(186)
<223> OTHER INFORMATION: Sequence replacing removed SacI site
<221> NAME/KEY: misc_feature
<222> LOCATION: (745)..(750)
<223> OTHER INFORMATION: Stop codons added by PCR primer

<400> SEQUENCE: 2
```

| atgaaaagaa tagtgccaaa gttcactgaa atcttccccg tggaggacgc gaactaccct | 60 |
| tacagcgcct tcatcgcgtc ggtccggaaa gacgtgatca acactgcac cgaccataaa | 120 |
| gggatcttcc agcccgtgct gccaccggag aagaaggtcc cggagctatg gttctacaca | 180 |
| gaactgaaaa ctaggaccag ctccatcacg ctcgccatac gcatggacaa cctgtacctc | 240 |
| gtgggcttca ggaccccggg cggggtgtgg tgggagttcg gcaaggacgg cgacacccac | 300 |
| ctcctcggcg acaaccccag gtggctcggc ttcggcggca ggtaccagga cctcatcggc | 360 |
| aacaagggtc tggagaccgt caccatgggc cgcgccgaaa tgaccagggc cgtcaacgac | 420 |
| ctggcgaaga agaagaaggc ggctgaccca caggccgaca cgaagagcaa gctggtgaag | 480 |
| ctggtggtca tggtgtgcga ggggctgcgg ttcaacaccg tgtcccgcac ggtggacgcg | 540 |
| gggttcaaca gccagcacgg ggtgaccttg accgtgacgc aggggaagca ggtgcagaag | 600 |
| tgggacagga tctccaaggc ggccttcgag tgggctgacc accccaccgc tgtgatcccc | 660 |
| gacatgcaga agcttggcat caaggataag aacgaagcag cgaggatcgt tgcgctcgtt | 720 |
| aagaatcaaa ctactgccgc tgcctaataa | 750 |

```
<210> SEQ ID NO 3
<211> LENGTH: 444
<212> TYPE: DNA
<213> ORGANISM: Zea mays
<220> FEATURE:
<221> NAME/KEY: misc_feature
<222> LOCATION: (1)..(3)
<223> OTHER INFORMATION: Initiation codon added by PCR primer
<221> NAME/KEY: mutation
<222> LOCATION: (181)..(186)
<223> OTHER INFORMATION: Sequence replacing removed SacI site
<221> NAME/KEY: misc_feature
<222> LOCATION: (439)..(444)
<223> OTHER INFORMATION: Stop codons added by PCR primer

<400> SEQUENCE: 3
```

| atgaaaagaa tagtgccaaa gttcactgaa atcttccccg tggaggacgc gaactaccct | 60 |
| tacagcgcct tcatcgcgtc ggtccggaaa gacgtgatca acactgcac cgaccataaa | 120 |
| gggatcttcc agcccgtgct gccaccggag aagaaggtcc cggagctatg gttctacaca | 180 |
| gaactgaaaa ctaggaccag ctccatcacg ctcgccatac gcatggacaa cctgtacctc | 240 |

```
gtgggcttca ggaccccggg cggggtgtgg tgggagttcg gcaaggacgg cgacacccac      300
ctcctcggcg acaaccccag gtggctcggc ttcggcggca ggtaccagga cctcatcggc      360
aacaagggtc tggagaccgt caccatgggc cgcgccgaaa tgaccagggc cgtcaacgac      420
ctggcgaaga agaagaagta ataa                                             444
```

<210> SEQ ID NO 4
<211> LENGTH: 354
<212> TYPE: DNA
<213> ORGANISM: Zea mays
<220> FEATURE:
<221> NAME/KEY: misc_feature
<222> LOCATION: (1)..(3)
<223> OTHER INFORMATION: Initiation codon added by PCR primer
<221> NAME/KEY: misc_feature
<222> LOCATION: (349)..(354)
<223> OTHER INFORMATION: Stop codons added by PCR primer

<400> SEQUENCE: 4

```
atggcggctg acccacaggc cgacacgaag agcaagctgg tgaagctggt ggtcatggtg       60
tgcgaggggc tgcggttcaa caccgtgtcc cgcacggtgg acgcggggtt caacagccag      120
cacggggtga ccttgaccgt gacgcagggg aagcaggtgc agaagtggga caggatctcc      180
aaggcggcct tcgagtgggc tgaccacccc accgctgtga tccccgacat gcagaagctt      240
ggcatcaagg ataagaacga agcagcgagg atcgttgcgc tcgttaagaa tcaaactact      300
gccgctgccg ctactgctgc cagtgctgac aacgacgacg acgaggccta ataa            354
```

<210> SEQ ID NO 5
<211> LENGTH: 43
<212> TYPE: DNA
<213> ORGANISM: Artificial Sequence
<220> FEATURE:
<223> OTHER INFORMATION: Description of Artificial Sequence: ProRIPBF
     primer
<221> NAME/KEY: misc_feature
<222> LOCATION: (1)..(19)
<223> OTHER INFORMATION: Introduced restriction sites

<400> SEQUENCE: 5

```
actcgagtct agaggatcca tggccgagat aaccctagag ccg                         43
```

<210> SEQ ID NO 6
<211> LENGTH: 49
<212> TYPE: DNA
<213> ORGANISM: Artificial Sequence
<220> FEATURE:
<223> OTHER INFORMATION: Description of Artificial Sequence: ProRIPSR
     primer
<221> NAME/KEY: misc_feature
<222> LOCATION: (1)..(19)
<223> OTHER INFORMATION: Introduced restriction sites

<400> SEQUENCE: 6

```
gactagtgtc gacgagctct tattaggcct cgtcgtcgtc gttgtcagc                   49
```

<210> SEQ ID NO 7
<211> LENGTH: 47
<212> TYPE: DNA
<213> ORGANISM: Artificial Sequence
<220> FEATURE:
<223> OTHER INFORMATION: Description of Artificial Sequence: RIP1BF primer
<221> NAME/KEY: misc_feature
<222> LOCATION: (1)..(19)
<223> OTHER INFORMATION: Introduced restriction sites

```
<400> SEQUENCE: 7
gctcgagtct agaggatcca tgaaaagaat agtgccaaag ttcactg          47

<210> SEQ ID NO 8
<211> LENGTH: 53
<212> TYPE: DNA
<213> ORGANISM: Artificial Sequence
<220> FEATURE:
<223> OTHER INFORMATION: Description of Artificial Sequence: RIP2SR
      primer
<221> NAME/KEY: misc_feature
<222> LOCATION: (1)..(19)
<223> OTHER INFORMATION: Introduced restriction sites

<400> SEQUENCE: 8
gactagtgtc gacgagctct tattaggcag cggcagtagt ttgattctta acg   53

<210> SEQ ID NO 9
<211> LENGTH: 53
<212> TYPE: DNA
<213> ORGANISM: Artificial Sequence
<220> FEATURE:
<223> OTHER INFORMATION: Description of Artificial Sequence: RIP1SR
      primer
<221> NAME/KEY: misc_feature
<222> LOCATION: (1)..(19)
<223> OTHER INFORMATION: Introduced restriction sites

<400> SEQUENCE: 9
aactagtgtc gacgagctct tattacttct tcttcttcgc caggtcgttg acg   53

<210> SEQ ID NO 10
<211> LENGTH: 51
<212> TYPE: DNA
<213> ORGANISM: Artificial Sequence
<220> FEATURE:
<223> OTHER INFORMATION: Description of Artificial Sequence: RIP2BF
      primer
<221> NAME/KEY: misc_feature
<222> LOCATION: (1)..(19)
<223> OTHER INFORMATION: Introduced restriction sites

<400> SEQUENCE: 10
actcgagtct agaggatcca tggcggctga cccacaggcc gacacgaaga g      51

<210> SEQ ID NO 11
<211> LENGTH: 42
<212> TYPE: DNA
<213> ORGANISM: Artificial Sequence
<220> FEATURE:
<223> OTHER INFORMATION: Description of Artificial Sequence: RIPCDF
      primer

<400> SEQUENCE: 11
gacctggcga agaagaagaa ggcggctgac ccacaggccg ac                42

<210> SEQ ID NO 12
<211> LENGTH: 42
<212> TYPE: DNA
<213> ORGANISM: Artificial Sequence
<220> FEATURE:
<223> OTHER INFORMATION: Description of Artificial Sequence: RIPCDR
      primer

<400> SEQUENCE: 12
gtcggcctgt gggtcagccg ccttcttctt cttcgccagg tc                42
```

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence: RIPSDF
      primer
<221> NAME/KEY: mutation
<222> LOCATION: (22)..(27)
<223> OTHER INFORMATION: Nucleotides modified to remove SacI site

<400> SEQUENCE: 13
ccggagctat ggttctacac agaactgaaa actaggacca gctcc                45

<210> SEQ ID NO 14
<211> LENGTH: 45
<212> TYPE: DNA
<213> ORGANISM: Artificial Sequence
<220> FEATURE:
<223> OTHER INFORMATION: Description of Artificial Sequence: RIPSDR
      primer
<221> NAME/KEY: mutation
<222> LOCATION: (19)..(24)
<223> OTHER INFORMATION: Nucleotides modified to remove SacI site

<400> SEQUENCE: 14
ggagctggtc ctagttttca gttctgtgta gaaccatagc tccgg                45

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: SUB21
      primer

<400> SEQUENCE: 15
ctcttgcttg aattcggact a                                          21

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: SUB25 primer

<400> SEQUENCE: 16
tagtccgaat tcaagcaaga gcaca                                      25

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: LDT15
      primer

<400> SEQUENCE: 17
gacagaagcg gatccttttt tttttttttt                                 30

<210> SEQ ID NO 18
<211> LENGTH: 381
<212> TYPE: DNA
<213> ORGANISM: Nicotiana tabacum

<400> SEQUENCE: 18
tctagaaagc ttatctaaac aaagttttaa attcatttct taaacgtcca ttacaatgta  60

-continued

```
atataactta gtcgtctcaa ttaaaccatt aatgtgaaat ataaatcaaa aaaagccaaa    120
gggcggtggg acggcgccaa tcatttgtcc tagtccactc aaataaggcc catggtcggc    180
aaaaccaaac acaaaatgtg ttatttttaa ttttttcctc ttttattgtt aaagttgcaa    240
aatgtgttat ttttggtaag accctatgga tatataaaga caggttatgt gaaacttgga    300
aaaccatcaa gttttaagca aaaccctctt aagaacttaa attgagcttc ttttggggca    360
tttttctagt gagaaggatc c                                              381
```